US 6,447,512 B1

(12) United States Patent
Landry et al.

(10) Patent No.: US 6,447,512 B1
(45) Date of Patent: Sep. 10, 2002

(54) INSTRUMENT AND METHOD FOR IMPLANTING AN INTERBODY FUSION DEVICE

(75) Inventors: Michael E. Landry, Austin, TX (US); Erik J. Wagner, Austin, TX (US); Stephen H. Hochshuler, Dallas, TX (US); John M. Larsen, Westlake Village, CA (US)

(73) Assignee: Spinal Concepts, Inc., Austin, TX (US)

( * ) Notice: Subject to any disclaimer, the term of this patent is extended or adjusted under 35 U.S.C. 154(b) by 0 days.

(21) Appl. No.: 09/478,923

(22) Filed: Jan. 6, 2000

(51) Int. Cl.⁷ .............................................. A61B 17/56
(52) U.S. Cl. ........................ 606/61; 606/80; 623/17.11
(58) Field of Search ........................ 606/60, 61, 62, 606/72–79; 623/17.11

(56) References Cited

U.S. PATENT DOCUMENTS

| | | |
|---|---|---|
| 3,848,601 A | 11/1974 | Ma et al. |
| 4,401,112 A | 8/1983 | Rezaian |
| 4,501,269 A | 2/1985 | Bagby |
| 4,714,469 A | 12/1987 | Kenna |
| 4,743,146 A | 5/1988 | Khmelnitsky et al. |
| 4,743,256 A | 5/1988 | Brantigan |
| 4,834,757 A | 5/1989 | Brantigan |
| 4,856,503 A | 8/1989 | Schelhas |
| 4,863,476 A | 9/1989 | Sheppard |

(List continued on next page.)

FOREIGN PATENT DOCUMENTS

| | | | |
|---|---|---|---|
| DE | 43 23 956 | 10/1994 | |
| EP | 0 260 044 | 3/1988 | |
| EP | 0 307 241 | 3/1989 | |
| EP | 0 880 938 | 12/1998 | |
| ES | 9500308 | 2/1995 | |
| FR | 2 717 068 | 9/1995 | |
| SU | 1424826 | 9/1988 | |
| WO | 97/00054 | 1/1997 | |
| WO | 97/06753 | 2/1997 | |
| WO | 98/17208 | 4/1998 | |
| WO | WO98/17209 | * 4/1998 | ................. 606/61 |
| WO | 98/17209 | 4/1998 | |
| WO | 98/55052 | 12/1998 | |
| WO | WO/9952453 | * 10/1999 | |
| WO | 99/52453 | 10/1999 | |

OTHER PUBLICATIONS

International Search Report, PCT/US 01/00451, May 1, 2001.
Albee et al., *Bone Graft Surgery in Disease, Injury and Deformity*, D. Appleton–Century Co., Inc., 1940, pp. xi–xv, 1–31, 48–107, and 210–227.

(List continued on next page.)

*Primary Examiner*—Pedro Philogene
(74) *Attorney, Agent, or Firm*—Eric B. Meyertons; Conley, Rose & Tayon, P.C.

(57) ABSTRACT

A holder is provided which couples to the spine. In an embodiment, the holder has two conduits into which sleeves may be inserted during a spinal fusion procedure. The holder may have a distractor extending from the bottom of the holder. The distractor secures the holder to the spine and maintains a proper separation distance between adjacent vertebrae. The sides of the distractor may be serrated to better secure the holder to the spine. The sleeves and conduits serve as alignment guides for instruments and implants used during the procedure. In an embodiment, the holder may include holes for fasteners that fixably secure the holder to vertebrae adjacent to a disk space. A flange may be placed around the holder to shield surrounding tissue and to provide a placement location for adjacent blood vessels during the spinal fusion procedure.

525 Claims, 18 Drawing Sheets

U.S. PATENT DOCUMENTS

| | | |
|---|---|---|
| 4,877,020 A | 10/1989 | Vich |
| 4,878,915 A | 11/1989 | Brantigan |
| 4,904,261 A | 2/1990 | Dove et al. |
| 4,936,848 A | 6/1990 | Bagby |
| 4,950,296 A | 8/1990 | McIntyre |
| 4,961,740 A | 10/1990 | Ray et al. |
| 5,015,247 A | 5/1991 | Michelson |
| 5,015,255 A | 5/1991 | Kuslich |
| 5,026,373 A | 6/1991 | Ray et al. |
| 5,055,104 A | 10/1991 | Ray |
| 5,112,354 A | 5/1992 | Sires |
| 5,123,926 A | 6/1992 | Pisharodi |
| 5,147,402 A | 9/1992 | Bohler et al. |
| 5,171,278 A | 12/1992 | Pisharodi |
| 5,192,327 A | 3/1993 | Brantigan |
| 5,263,953 A | 11/1993 | Bagby |
| 5,306,307 A | 4/1994 | Senter et al. |
| 5,306,309 A | 4/1994 | Wagner et al. |
| 5,336,240 A | 8/1994 | Metzler et al. |
| 5,370,697 A | 12/1994 | Baumgartner |
| 5,390,683 A | 2/1995 | Pisharodi |
| 5,397,364 A | 3/1995 | Kozak et al. |
| 5,425,772 A | 6/1995 | Brantigan |
| 5,443,514 A | 8/1995 | Steffee |
| 5,458,638 A | 10/1995 | Kuslich et al. |
| 5,484,437 A * | 1/1996 | Michelson .................... 606/61 |
| 5,489,307 A | 2/1996 | Kuslich et al. |
| 5,489,308 A | 2/1996 | Kuslich et al. |
| 5,505,732 A * | 4/1996 | Michelson .................... 606/61 |
| 5,522,899 A | 6/1996 | Michelson |
| 5,536,271 A | 7/1996 | Daly et al. |
| 5,571,192 A | 11/1996 | Schönhöffer |
| 5,593,409 A | 1/1997 | Michelson |
| 5,601,556 A | 2/1997 | Pisharodi |
| 5,607,424 A | 3/1997 | Tropiano |
| 5,609,635 A | 3/1997 | Michelson |
| 5,609,636 A | 3/1997 | Kohrs et al. |
| 5,632,747 A | 5/1997 | Scarborough et al. |
| 5,645,598 A | 7/1997 | Brosnahan, III |
| 5,653,763 A | 8/1997 | Errico et al. |
| 5,658,337 A | 8/1997 | Kohrs et al. |
| 5,665,122 A | 9/1997 | Kambin |
| 5,669,909 A | 9/1997 | Zdeblick et al. |
| 5,674,295 A | 10/1997 | Ray et al. |
| 5,674,296 A | 10/1997 | Bryan et al. |
| 5,676,701 A | 10/1997 | Yuan et al. |
| 5,683,394 A | 11/1997 | Rinner |
| 5,688,279 A | 11/1997 | McNulty et al. |
| 5,693,100 A | 12/1997 | Pisharodi |
| 5,697,977 A | 12/1997 | Pisharodi |
| 5,700,291 A | 12/1997 | Kuslich et al. |
| 5,702,391 A | 12/1997 | Lin |
| 5,702,449 A | 12/1997 | McKay |
| 5,702,450 A | 12/1997 | Bisserie |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,709,683 A | 1/1998 | Babgy |
| 5,713,899 A | 2/1998 | Marnay et al. |
| 5,716,359 A | 2/1998 | Ojima et al. |
| 5,716,415 A | 2/1998 | Steffee |
| 5,716,416 A | 2/1998 | Lin |
| 5,720,746 A | 2/1998 | Soubeiran |
| 5,720,748 A | 2/1998 | Kuslich et al. |
| 5,722,977 A | 3/1998 | Wilhelmy |
| 5,741,253 A | 4/1998 | Michelson |
| 5,749,916 A | 5/1998 | Richelsoph |
| 5,766,253 A | 6/1998 | Brosnahan, III |
| 5,772,661 A | 6/1998 | Michelson |
| 5,776,199 A | 7/1998 | Michelson |
| 5,782,919 A | 7/1998 | Zdeblick et al. |
| 5,785,710 A | 7/1998 | Michelson |
| 5,797,909 A * | 8/1998 | Michelson |
| 5,797,917 A | 8/1998 | Boyd et al. |
| 5,814,084 A | 9/1998 | Grivas et al. |
| 6,042,582 A * | 3/2000 | Ray ........................... 606/61 |
| 6,080,155 A * | 6/2000 | Michelson .................... 606/61 |
| 6,083,228 A | 7/2000 | Michelson |
| 6,096,038 A | 8/2000 | Michelson |
| 6,113,602 A * | 9/2000 | Sand |

OTHER PUBLICATIONS

Vich, "Update of the Cloward procedure: new instruments," J. Neurosurg., vol. 81, Nov. 1994, pp. 716–720.

Vich, "Anterior cervical interbody fusion with threaded cylindrical bone," J. Neurosurg., vol. 63, Nov. 1985, pp. 750–753.

"Introducing the EndoDowel™," Musculoskeletal Transplant Foundation, Oct. 1996.

Catalog from Musculoskeletal Transplant Foundation, Apr. 1996.

"The MTF EndoDowel™," Musculoskeletal Transplant Foundation, 1996.

"Laparoscopic Bone Dowel Instruments," Sofamor Danek, 1995.

"Laparoscopic Bone Dowel Surgical Technique," Sofamor Danek, 1995.

Brantigan et al, "A Carbon Fiber Implant of Aid Interbody Lumbar Fusion (Mechanical Testing," Spine, vol. 16, No. 6 Supplement, 1991.

"Trends in Spine & Disc Surger," MedPro Month, Nov. 1996.

Wittenberg et al., "Compressive Strength of Autologous and Allogenous Bone Grafts for Thoracolumbar and Cervical Spine Fusion," Spine, vol. 15, No. 10, 1990, pp. 1073–1078.

"Spinal Fusion Surgery and The BAK™ Interbody Fusion System," Spine Tech, Inc., 1993.

"BAK®/Cervical Interbody Fusion System," Spine Tech, Inc., 1994.

"The BAK™ Interbody Fusion System," Spine Tech, Inc., 1996.

"BAK™ Interbody Fusion System (Porosity)," Spine Tech, Inc., 1996.

"BAK™ Interbody Fusion System (Biomechanics)," Spine Tech, Inc., 1996.

"BAK™ Interbody Fusion System (Instrumentation)," Spine Tech, Inc., 1996.

"Bone Harvester," Spine Tech, Inc., 1996.

"Biomechanical Rationale, The BAK™ Interbody Fusion System: An Innovative Solution," Spine Tech, Inc., 1994.

"Surgical Technique using Bone Dowel Instrumentation, for Anterior Approach," Sofamor Danek, 1996.

"Surgical Technique using Bone Dowel Instrumentation, for Posterior Approach," Sofamor Danek, 1996.

Catalog from Cloward© Instruments, 1996.

White et al., *Clinical Biomechanics of the Spine*, J.B. Lippincott Co., 1978, White et al., 1990, 551–552.

Hochschuler et al, "Compressive Strength of Hollow, Allograft Bone Cylinders Proposed for Lumbar Interbody Fusion," NASS 8th Annual Meeting, Oct. 1993.

"MD–I™ and MD–II™ Custom Machined Cortical Dowels," University of Florida Tissue Bank, 1996.

"MD–III™ Threaded Cortical Dowel, Design Rationale and Surgical Technique," University of Florida Tissue Bank, 1997.

"Operative Treatment of Degenerative Cervical Disk Disease," Journal of the Southern Orthopaedic Association, 1996.

"Ray Threaded Fusion Cage, Surgical Technique Manual," Surgical Dynamics, 1996.

"Ray Threaded Fusion Cage," Surgical Dynamics, 1996.

"Surgeons First in Region to Use Lumbar Cage for Spinal Disc Disease," Hohmann Enterprises, 1996.

Heim et al, "The Treatment of Lumbar Degenerative Motion Segment Pain," Spinal Frontiers, Jun. 1997.

"Threaded Bone Dowel," Hohmann Enterprises, 1997.

Technical Monograph, Threaded Cortical Dowel, "Mechanical Characteristics and Evaluation," University of Florida Tissue Bank, 1996.

"Tyler Neurosurgeon Jon T. Ledlie, MD, Introduces Bone Dowel Procedures for East Texas–Area Back Pain Sufferers," Tyler Neurosurgical Assoc., 1998.

"Tyler Neurosurgeon Jon T. Ledlie, MD, Introduces Laparoscopic Procedure for East Texas Back Pain Sufferers," Tyler Neurosurgical Assoc., 1998.

"Vertigraft™ Textured Allograft Bone Graft," LifeNet, 1998.

"New Approaches to Spine Surgery," USC University Hospital Quarterly, vol. 10, No. 3, 1998.

Beadling, "FDA clears spinal cages for interbody lumbar fusion," Orthopedics Today, vol. 16, No. 10, Oct. 1996, pp. 24–25.

International Search Report, Application No. PCT/US98/08832, mailed Sep. 1, 1998.

* cited by examiner

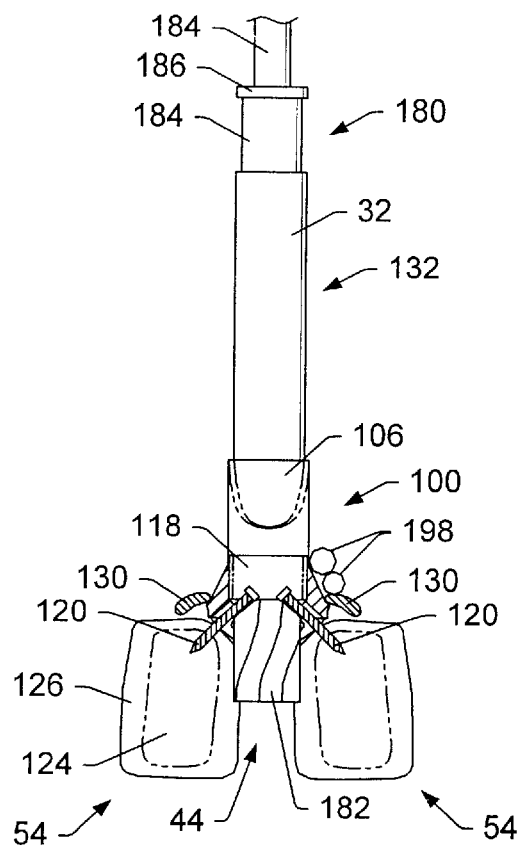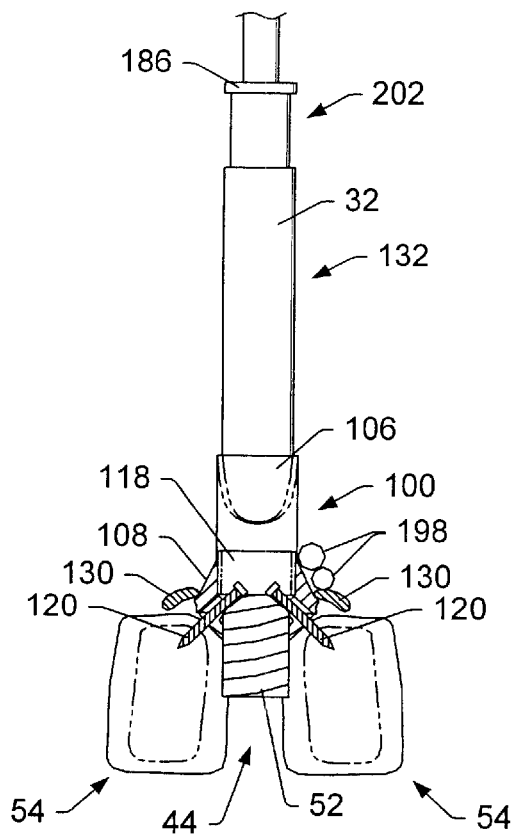
FIG. 28dFIG. 28e

INSTRUMENT AND METHOD FOR IMPLANTING AN INTERBODY FUSION DEVICE

BACKGROUND OF THE INVENTION

1. Field of the Invention

The present invention generally relates to spinal fixation and fusion systems. The invention also generally relates to an insertion guide used during the insertion of a spinal implant system, wherein the implant system is used for correction, fixation, and/or stabilization of the spine.

2. Description of the Related Art

Intervertebral disks that become degenerated due to various factors such as trauma or aging typically have to be partially or fully removed. Removal of an intervertebral disk can destabilize the spine, making it necessary to replace the vertebral disk to maintain the height of the spine and to fuse the spine. Spinal implants are often used to prevent collapse of the spine. In a typical spinal fusion procedure, an intervertebral disk is removed and implants are inserted in the disk space between neighboring vertebrae. The implants maintain normal disk spacing and help restore spinal stability.

The implants may be constructed of any biocompatible materials sufficiently strong to maintain spinal distraction including, but not limited to, bone, stainless steel, or inert metals. Implants are typically packed with bone graft or a synthetic bone graft substitute to facilitate spinal fusion. Implants may have a variety of shapes, which include, but are not limited to, threaded cylinders, unthreaded cylinders, and parallelepipeds.

An anterior spinal fusion procedure is often preferred to a posterior spinal fusion procedure. An anterior spinal fusion procedure may require less bone removal and muscle distraction than a posterior spinal fusion procedure. Also, an anterior spinal fusion procedure may involve less risk of nerve damage than a posterior spinal fusion procedure. In an anterior spinal fusion procedure, a surgical opening in the abdomen may be up to ten inches deep. A protective sleeve may be used during preparation and insertion of a spinal implant. The protective sleeve may serve to protect abdominal organs, blood vessels and other tissue during the spinal implant procedure. The sleeve typically extends above the surgical opening during use. The sleeve may maintain distraction of the vertebrae. Also, the sleeve may serve as an alignment guide for tool and implant insertion during the surgical procedure.

Protective sleeves typically have distractors on a distal end. Distractors are projections that may be inserted into a disk space during a spinal fusion procedure. The distractors may serve to achieve and maintain distraction of adjacent vertebrae. Distractors may also help to secure the protective sleeve to the spinal column during the procedure. Protective sleeves may have one tube or two parallel tubes. FIG. 1 shows a single-tube protective sleeve, and FIG. 2 shows a dual-tube protective sleeve.

FIG. 1 illustrates a single-tube protective sleeve 30 used in a spinal fusion procedure. A spinal fusion procedure involves the insertion of one or more implants in a disk space between two vertebrae. Protective sleeve 30 includes a substantially long, hollow tube 32, two distractors 34 on opposite sides of an end of the tube, and two spikes 36 (only one shown) on opposite sides of the end of the tube. Protective sleeve 30 is typically sufficiently long to allow access to a spinal column of a large patient during an anterior procedure. Protective sleeve 30 may also be used in a posterior spinal fusion procedure.

A spinal fusion procedure using implants typically involves the insertion of two implants that are bilaterally positioned in an intervertebral disk space. During an anterior procedure, the disk space is prepared by performing a discectomy and by distracting the vertebrae adjacent the disk space. A cap (not shown) is placed on end 38 of the protective sleeve 30 opposite distractors 34 to protect the end of the sleeve during insertion. Distractors 34 may then be hammered into the disk space by striking the cap with a mallet (not shown). Spikes 36 are hammered into disk bone on the vertebrae and help to stabilize protective sleeve 30 during the procedure. Distractors 34 serve to separate the adjoining vertebrae to approximately normal spacing.

After insertion, a hole is drilled in the disk space by inserting a tool with a reaming head attachment through tube 32 and rotating the tool until a predetermined depth is reached. In some procedures, the hole is then tapped by inserting a tool with tap head attachment through tube 32 and rotating the tool until a predetermined depth is reached. The top and bottom of the reamed and tapped hole may extend into the end plates of the adjacent vertebrae. After the hole is prepared, an implant may be inserted in the hole by attaching the implant to an implant insertion tool and inserting the implant through tube 32. For untapped holes, the implant may be hammered into the hole by striking the implant insertion tool with a mallet. For tapped holes, the implant may be threaded into the hole by turning the implant insertion tool. Then, the protective sleeve 30 may be removed.

If a second implant is to be inserted, the protective sleeve 30 is hammered in the disk space opposite the first implant and the procedure is repeated. Alternatively, the protective sleeve 30 may remain inserted in the disk space, and a second single-tube protective sleeve 30 may be inserted adjacent to the protective sleeve.

The optimal alignment and spacing of implants in a spinal fusion procedure may be determined before surgery. Achieving the predetermined alignment and spacing during surgery is often important for optimal fusing of the adjacent vertebrae. Protective sleeve 30 has characteristics that may make achieving alignment difficult. First, each of the two holes is aligned, reamed, and tapped in a separate procedure. It is often difficult to align and space the holes correctly. Second, the alignment of protective sleeve 30 must be maintained after insertion. Any slight movement of protective sleeve 30, which may act like a lever arm, may result in misalignment of the hole.

FIG. 2 illustrates a dual-tube protective sleeve 40 used in a spinal fusion procedure involving the insertion of two implants into a disk space. Protective sleeve 40 includes substantially long, hollow tubes 32, one or more distractors 34 and one or more spikes 36. Protective sleeve 40 is typically long enough to allow access during an anterior procedure to an intervertebral disk in a large patient. Spinal fusion using implants with protective sleeve 40 involves the insertion of two implants, bilaterally positioned in parallel in an intervertebral disk space. During an anterior procedure, the disk space is prepared by performing a discectomy and by distracting the vertebrae adjacent the disk space. A cap (not shown) is placed on the end 42 of protective sleeve 40 opposite distractor 34 to protect the sleeve during insertion. Distractor 34 is then hammered into the disk space by striking the cap with a mallet (not shown). Spikes 36 are hammered into disk bone on the adjacent vertebrae to help stabilize protective sleeve 40 during the procedure. Distractor 34 serves to separate the adjoining vertebrae to approximately normal spacing. After insertion, holes are reamed in the disk space by inserting a tool with a reaming head attachment through tubes 32 and rotating the tool until a predetermined depth is reached. In some procedures, the holes are tapped by inserting a tool with a tap head attachment through tubes 32 and rotating the tool until a predetermined depth is reached. The top and bottom of the reamed and tapped holes may extend into the end caps of the adjacent vertebrae. After the holes are prepared, implants are inserted in the holes by attaching the implants to an implant insertion tool and inserting the implants through tubes 32. For untapped holes, the implants are hammered into the hole by striking the implant insertion tool with a mallet. For tapped holes, the implants are threaded into the holes by turning the implant insertion tool. After both implants are inserted, protective sleeve 40 is removed.

FIG. 3 shows a representation of implants inserted into disk space 44 using a dual-tube protective sleeve 40. Spinal nerves in the spinal canal 46 are protected by dura 48. Nerves 50 extend from the spinal canal 46. Implants 52 are inserted between two vertebrae 54 (one shown). Care must be taken during insertion of the implants 52 to make sure that the implants do not impinge on the nerves 50.

Like single-tube protective sleeve 30, dual-tube protective sleeve 40 has characteristics that make it difficult to align the implants correctly. First, the alignment of protective sleeve 40 must be maintained after insertion. Any slight movement of sleeve 40, which may act like a lever arm, may result in misalignment of the hole. Second, the long parallel tubes make it difficult to angulate the two implants 52 relative to each other. Angulated implants may be the desired alignment in some spinal fusion procedures. Using a dual-tube protective sleeve 40 has the advantage that the surgical procedure is simplified because there is only one insertion procedure, as opposed to two insertion procedures for a single-tube protective sleeve 30.

Single- and dual-tube protective sleeves share some disadvantages. First, the sleeves are typically unitary members that are long enough to extend out of a ten-inch deep surgical opening after being hammered into place. To maintain alignment after insertion, the sleeve must be kept as motionless as possible. The sleeve tends to act like a lever arm, and any slight motion of the sleeve during the procedure may result in misalignment of the implants. The sleeve acting as a lever arm is particularly problematic when the sleeve is handed off during the surgical procedure from one member of the surgical team to another member of the surgical team.

A second disadvantage of protective sleeves is related to the first disadvantage. The sleeve is held in place only by the distractors and the spikes inserted in the disk space. This connection may not be very secure. Because the connection is not secure, the sleeve may have to be held by the members of the surgical team throughout the entire procedure to maintain proper alignment. As noted above, any slight movement can result in the misalignment of the implants.

A third disadvantage of protective sleeves is that they may afford minimal protection to surrounding tissues during a spinal fusion procedure. Major blood vessels, parallel the anterior surface of the spine for much of the spine's lower length. These vessels may be retracted during the procedure. The interface between the distal end of the sleeve and the spinal column is typically not a perfect fit. Gaps may exist between the sleeve and the vertebrae. The presence of gaps creates the risk of drill bits, taps, and implants coming into contact with the blood vessels or other surrounding tissues during the procedure. Also, the blood vessels may be pinched between the sleeve and the vertebrae. A nick or cut to either the aorta or the blood vessels can be life threatening.

The above-mentioned methods and systems inadequately address the need to angulate implants in some spinal fusion procedures, the need to maintain precise alignment throughout the procedure, and the need to protect surrounding tissues during the procedure. It is therefore desirable that an improved method and system be derived for inserting spinal implants during a spinal fusion procedure.

SUMMARY OF THE INVENTION

A holder or base may be used to insert instruments and/or spinal implants into a disk space during a spinal fusion procedure. In an embodiment, distractors and tangs of a holder may be driven into an intervertebral disk space. The distractors and tangs may secure the holder to the spine during. In an embodiment, fasteners extending through a holder into the adjacent vertebrae may be used fix the holder to the spine. In another embodiment, distractors, tangs, and fasteners secure a holder to the spine. A flange may be placed around the holder to protect the surrounding tissue and blood vessels. Protective sleeves may be inserted into and may be removed from conduits in the holder. A portion of the sleeve may have a slot or a window, located adjacent to the top of the holder. The slot or window may serve as a view-port to provide increased visibility near the procedure site. Surgical instruments may be inserted through the protective sleeves and through the holder conduits to prepare the intervertebral space for an implant.

An embodiment of a holder includes a body, one or more conduits passing through the body from the top to the bottom, one or more distractors on the bottom of the body, and one or more tangs on the bottom of the body. The body may have a smooth outer surface with no sharp corners. In some embodiments, the body may be flared near the bottom to provide shielding for surrounding tissue. The flared bottom may provide room for optional fasteners to extend at oblique angles from the body of the holder. The flared body may also provide the holder with a stable base against the spinal column.

An optional flange may be provided that fits around the outer surface of the holder. The flange may provide shielding of soft tissue, such as blood vessels and organs, from cutting tools at the junction of the holder and the vertebral bodies. The flange may also prevent damage to soft tissues due to pinching of the soft tissue between the holder and the vertebral bodies. The flange may be made of a rigid or semi-rigid material. A portion of the flange may be made of an elastic material so that the flange may stretch over and slide down the holder. In one embodiment, the holder may include a rim for holding the flange in place after installation. In another embodiment, the holder may include a groove for holding the flange in place. In another embodiment, the flange has an elastic collar, which holds the flange in place against the holder.

In some embodiments, the inner surfaces of the conduits may contain shoulders to limit the insertion distance of protective sleeves in the conduits. Above a shoulder, a conduit may be sized to match the outer diameter of a protective sleeve. Below the shoulder, the conduit may be sized to match the outer diameter of instrument heads and implants to be used in the procedure. In some embodiments, the shoulder may include slots configured to engage distractors on protective sleeves; thus allowing the holder to be used with single-tube protective sleeves having distractors.

Embodiments of the holder may have non-circular conduits. The cross sectional shape of the holder conduits and the protective sleeves inserted into the holder may be any desired shape that allows for the insertion of spinal implants into a disk space. For example, the cross sectional shape of the conduits may be rectangular if the cross sectional shape of the spinal implants are generally rectangular. Other embodiments of the holder may have circular conduits or conduits which do not have a regular geometric shape. Embodiments of holders that have circular conduits may be constructed with conduits of different diameters to accommodate protective sleeves and implants of different diameters.

Embodiments of holders may be provided with non-parallel angled conduits. Non parallel conduits allow the insertion of implants at oblique angles to improve spinal fusion and to protect nerves posterior to the disk space. Other holder embodiments may have parallel conduits.

The distractors on the bottom of the holder body are projections that insert into a disk space during a spinal fusion procedure. The distractors may serve to achieve and/or maintain distraction of the adjacent vertebrae. The distractors may also secure the holder to the spinal column during the procedure. The distractors may be substantially wedge-shaped, and may include curved surfaces. The tangs on the bottom of the holder body may serve to maintain distraction, and may also maintain a parallel orientation of the vertebrae during the procedure. The tangs may also be substantially wedge-shaped, and may also include curved surfaces. Outer surfaces of the distractors and tangs may be serrated to secure the holder to adjacent vertebrae during a spinal fusion procedure.

In one embodiment, there is one distractor centrally located between two conduits; and two tangs, with one next to each conduit opposite the distractor. Curved inner surfaces on the tangs and curved surfaces on the distractor may serve as partially enclosed extensions of the conduits, and may help maintain alignment of the implant during a spinal fusion procedure.

In some embodiments, the body includes one or more fastener holes for the insertion of fasteners into vertebrae. The fastener holes may be angled so that fasteners inserted through the holes extend obliquely into adjacent vertebrae without damaging the vertebral endplates. The fasteners may pass through the end caps of the vertebrae into cancellous bone in the interior of the vertebrae. The fasteners may serve to substantially anchor the holder to the spine during the spinal fusion procedure.

The height of the holder, when inserted in a spine, may be substantially less than the length of a protective sleeve. During the spinal fusion procedure, a protective sleeve may be inserted into a holder conduit when needed and removed when not needed without affecting alignment. Removal of a protective sleeve from the holder decreases the likelihood of a protective sleeve being inadvertently used as a lever arm during the procedure. Removing a protective sleeve from the holder may increase visibility at the procedure site. Removing a protective sleeve may also allow for easy irrigation of the entire surgical site, including the holes being prepared for the implants.

The ability to remove the protective sleeves when not in use, the short profile of the holder, and the fastener anchoring system all help to maintain proper alignment during the insertion of implants in a spinal fusion procedure.

BRIEF DESCRIPTION OF THE DRAWINGS

Further advantages of the present invention will become apparent to those skilled in the art with the benefit of the following detailed description of embodiments and upon reference to the accompanying drawings in which:

FIGS. 28a–28e illustrate steps included in a spinal fusion procedure using an embodiment of a holder;

DESCRIPTION OF THE PREFERRED EMBODIMENTS

Figures 1, 2:
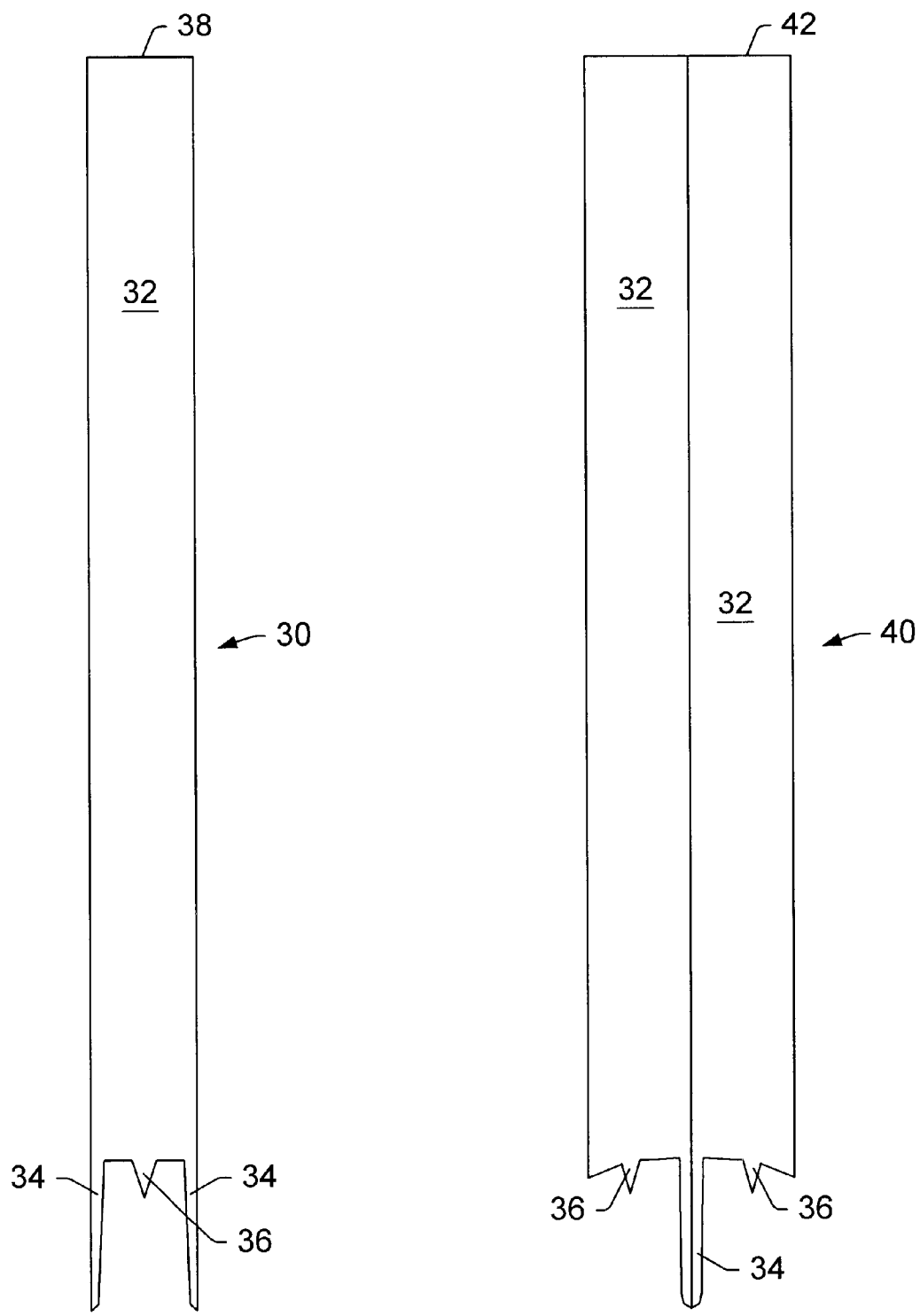
FIG. 1 illustrates a single-tube protective sleeve.
FIG. 2 illustrates a dual-tube protective sleeve.

Referring to the drawings, a holder or base for use as an insertion guide during a spinal implantation procedure is designated generally as 100. A holder may be used to support a sleeve during a spinal fusion procedure, and a base may be used with or without a sleeve during a spinal fusion procedure. For illustrative purposes only, the following description will describe a holder. A person having ordinary skill in the art will understand that a holder may be used as a base, and a base may be used as a holder.

FIGS. 4–10 show views of a first embodiment of the holder 100. The holder 100 may include unitary body 102, conduits 104 through the body, conduit extenders 106, flared portion 108, flange rim 110, holes 112, distractor 114, and tangs 116. The height of the holder body may be less than about six inches. Preferably, the holder height is less than four inches, and more preferably, less than 2 inches.

The conduits 104 may have circular cross sections. Alternatively, the conduits 104 may have any desired cross sectional shape, such as rectangular or ellipsoid, to correspond to instruments and implants used during a spinal fusion procedure.

Figure 6:
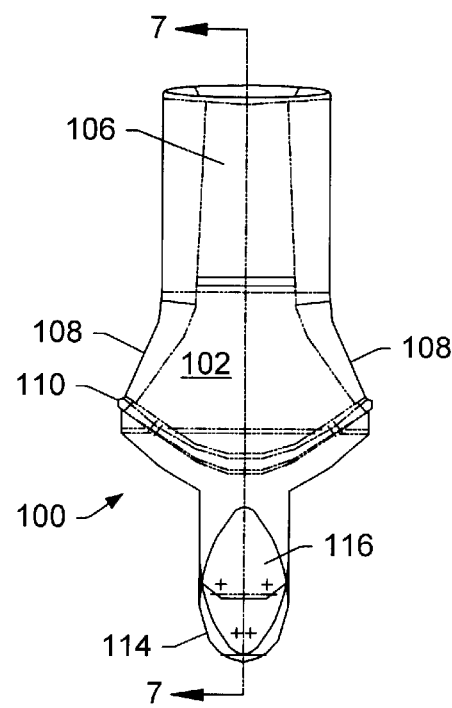
FIG. 6 is a side view the first embodiment holder.
Figure 8:
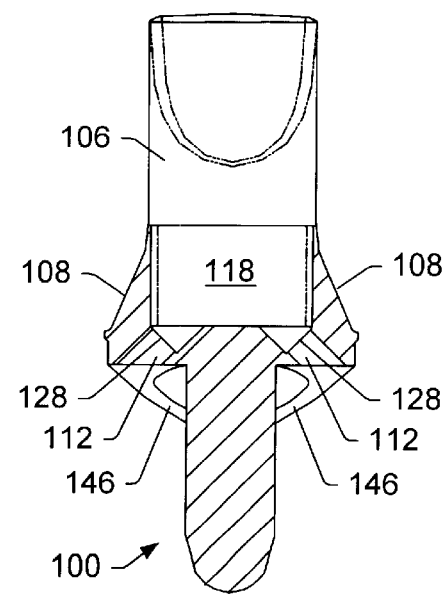
FIG. 8 is a cross-sectional view of the first embodiment holder taken substantially along line 8—8 of FIG. 5.
Figures 28A, 28B, 28C:
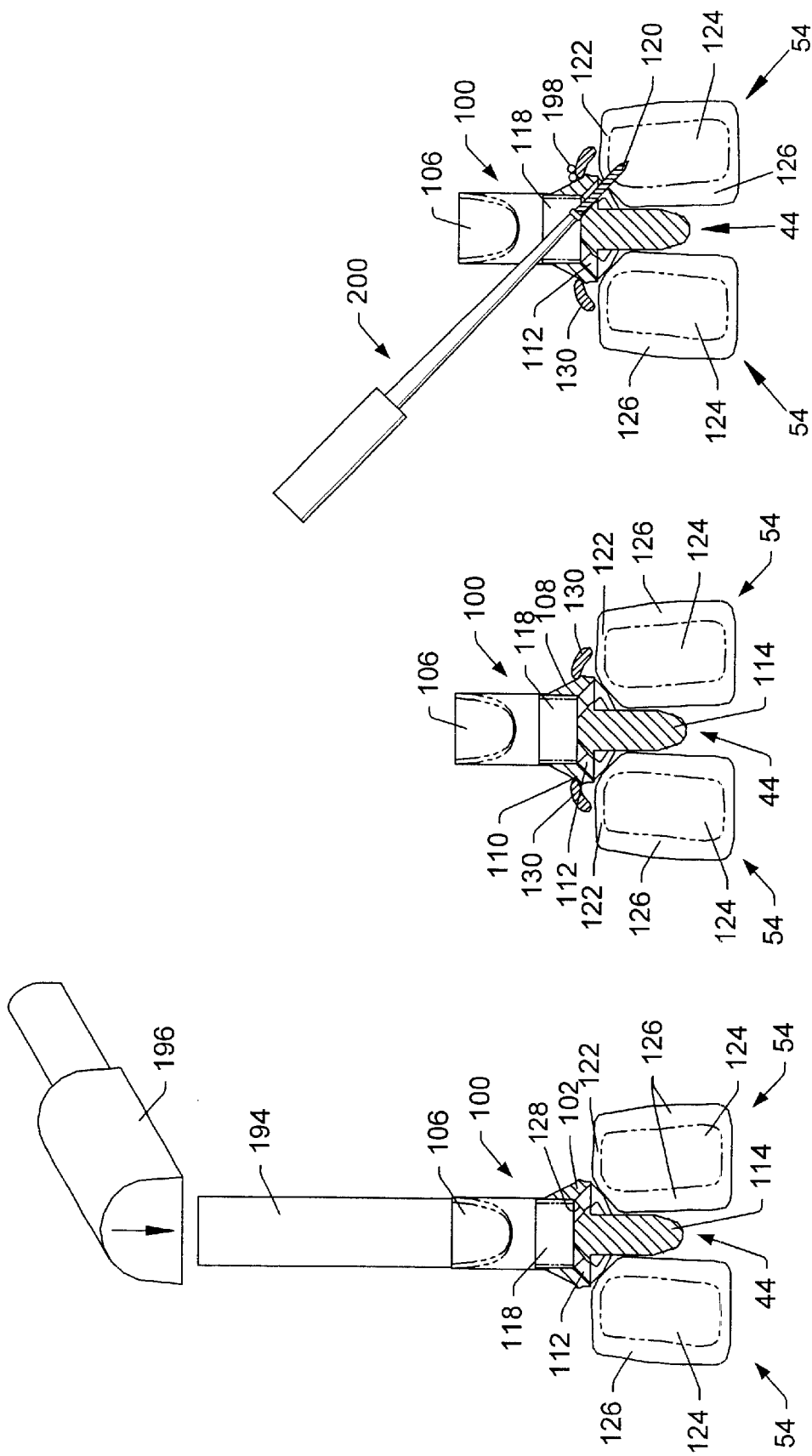

As shown in FIG. 6, the body 102 may have flared portion 108. The flared portion 108 may allow for angulation of fastener holes 112, as shown in FIG. 8. Fastener holes 112 may be located in slot 118. Angulated fastener holes 112 allow is fasteners 120 inserted through the fastener holes to penetrate adjacent vertebrae 54 through end caps 122 of the vertebrae and into cancellous bone 124, as shown in FIG. 28c. Attaching the holder 100 to the vertebrae 54 with fasteners 120 placed through end caps 122 may minimize weakening of the end plates 126 of the vertebrae. Shoulders 128 limit the insertion depth of the fasteners 120 into the holder 100. Fasteners 120 may be any type of fastening device including, but not limited to, screws, nails, rivets, trocars, pins, and barbs.

The flared portion 108 of the body 102 may shield blood vessels, nerves, and other soft tissue from damage by the body and tools used during the spinal fusion procedure. In addition, the flared portion 108 increases the circumference of holder 100 to a maximum near flange rim 110. Optional flange 130 may slip over the top of holder 100 and reside against the rim 110. The flared portion 108 may also provide a stable base on the end caps 122 of the vertebrae 54 for holder 100.

Figure 9:
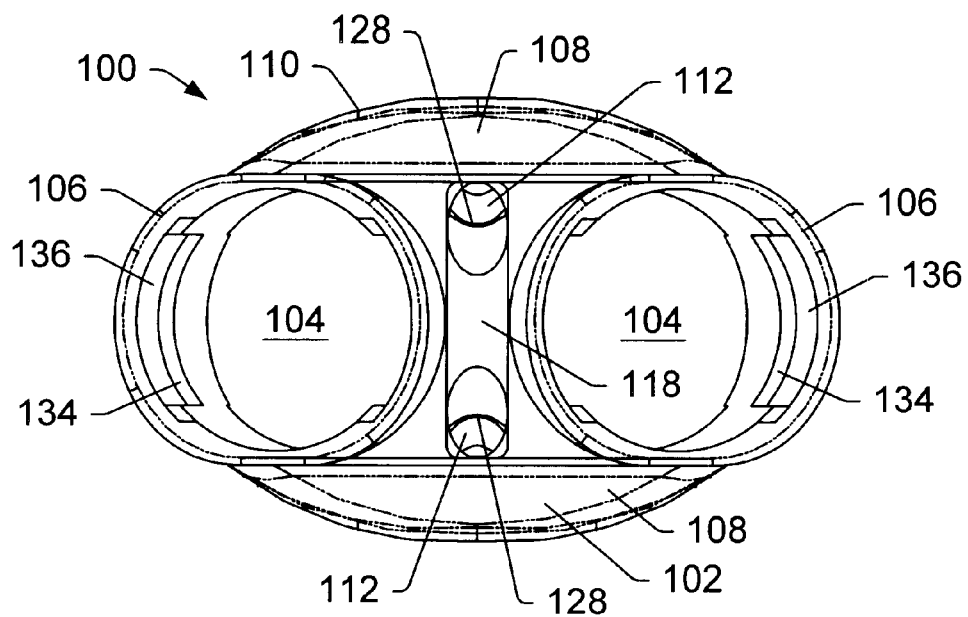
FIG. 9 is a top view of the first embodiment holder.
Figure 10:
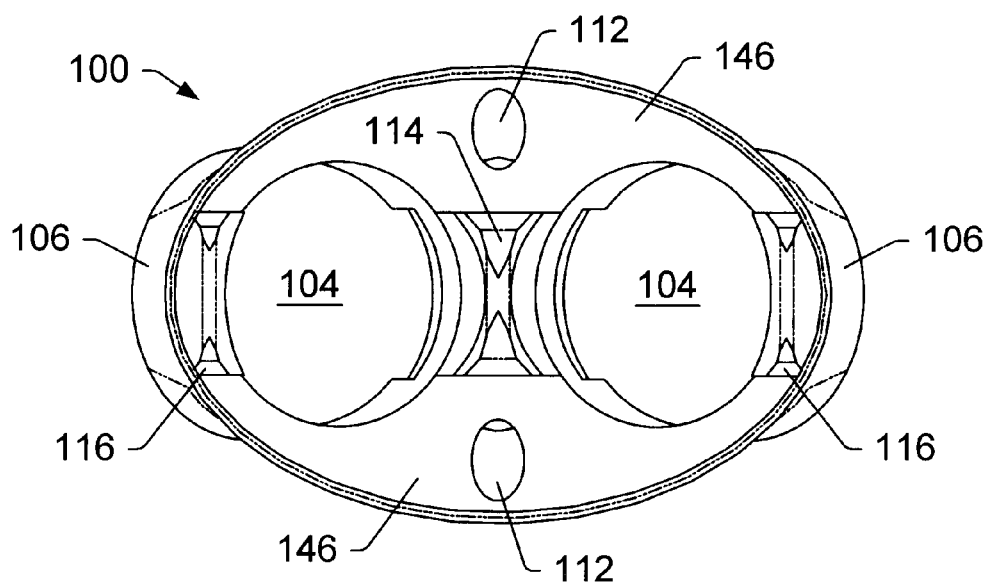
FIG. 10 is a bottom view of the first embodiment holder.
Figure 11:
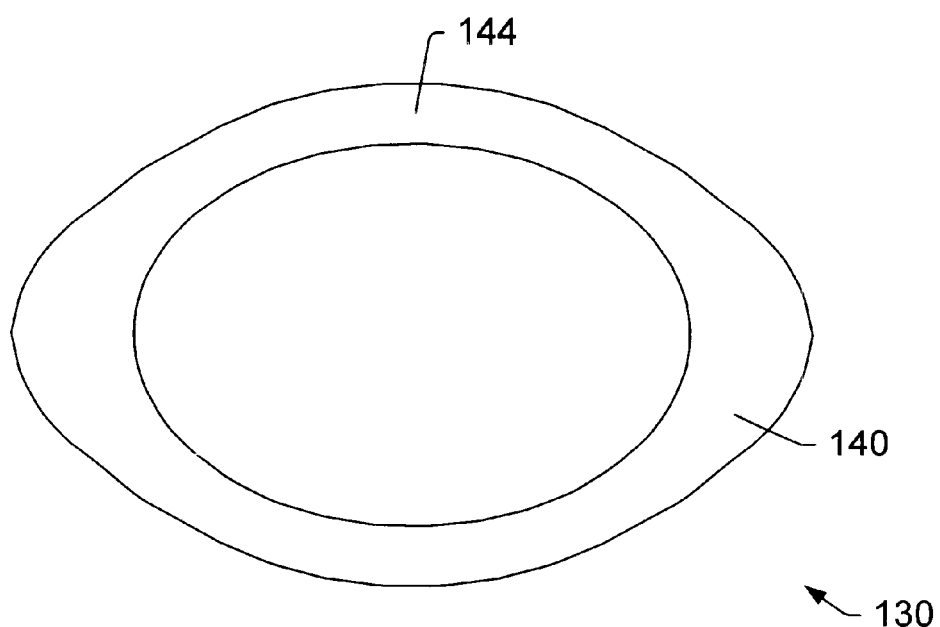
FIG. 11 is a top view of an embodiment of a holder flange.
Figure 12:
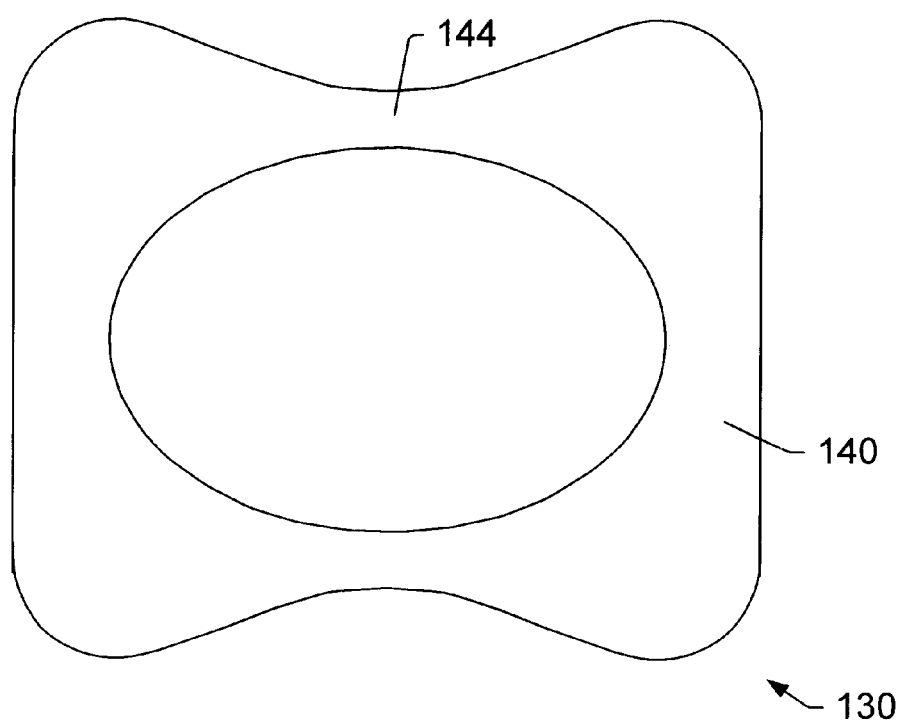
FIG. 12 is a top view of another embodiment of a holder flange.
Figure 13:
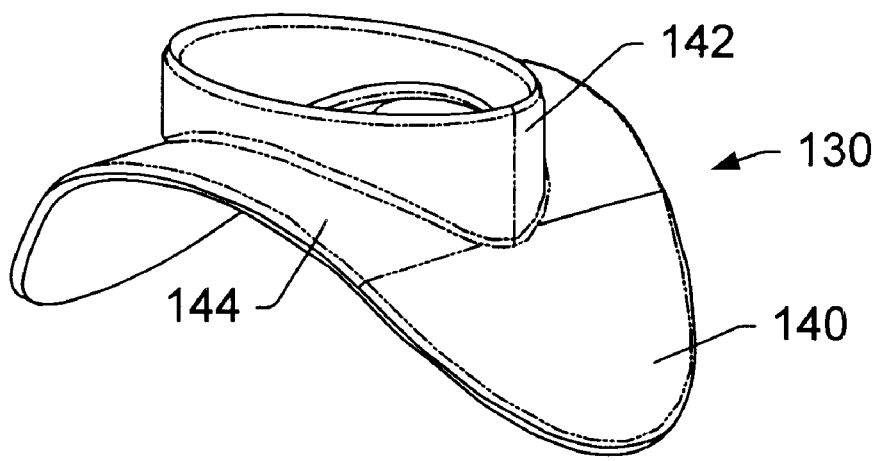
FIG. 13 is a perspective view of an embodiment of a holder flange with a collar.

The perimeter of the conduit 104 at a top end of the holder 100 may match the outer perimeter of protective sleeve 132 inserted into the conduit. The conduits 104 may include shoulders 134. A shoulder 134 prevents insertion of a protective sleeve 132 into a conduit 104 beyond a certain depth. As shown in FIG. 9 and in cross section in FIG. 7, a conduit 104 may include slots 136. The slots 136 correspond to the shape of the distractors 34 on the ends of single-tube protective sleeves 30. Slots 136 allow a holder 100 to be used with a single-tube protective sleeve 30 having distractors 34, such as the sleeve shown in FIG. 1. In other embodiments, conduits 104 may be configured to receive protective sleeves 132 without distractors 34 by having shoulders 128 which extend fully around the diameter of the conduits 104. A protective sleeve 132 may be slid into a conduit 104 without the use of an insertion tool.

Figure 7:
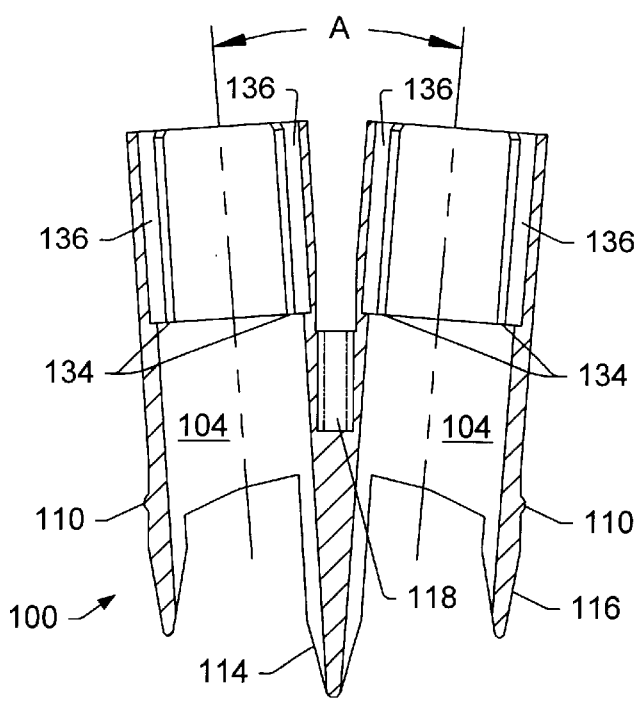
FIG. 7 is a cross-sectional view of the first embodiment holder taken substantially along line 7—7 of FIG. 6.

FIG. 7 shows a cross sectional view of the first embodiment holder 100 with the conduits 104 angulated toward one another. Having the conduits angled relative to one another allows for the angulation of implants 52. Angulated implants 52 may provide a more stable fusion of vertebrae 54. In addition, angulated implants 52 may be less likely to protrude from posterior side 138 of the disk space to press on nerves 50 exiting the spinal canal 46. The angle A, located between a center line of a first conduit 104 and a centerline of an adjacent conduit, may vary from 0 to about 30 degrees, preferably the angle A is less than about 20 degrees, and more preferably, the angle A is less than about 10 degrees. If the angle A is 0 degrees, then the adjacent conduits 104 are parallel.

Figure 14:
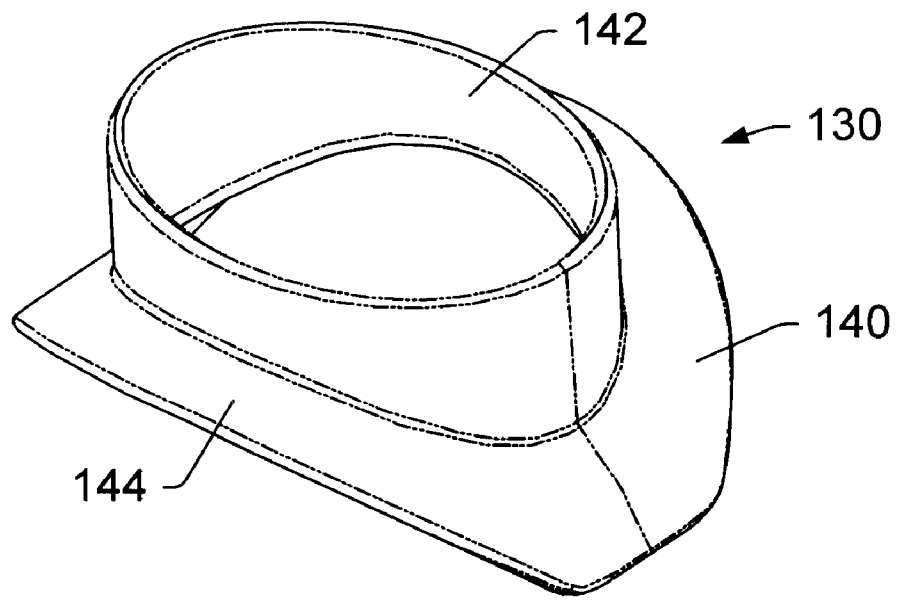
FIG. 14 is a perspective view of an embodiment of a holder flange.

Flange rim 110 may support flange 130. The flange 130 may serve to protect blood vessels and other tissue placed upon the flange 130 and near the body 102 of the holder 100. FIGS. 11–14 show some flange embodiments. In one embodiment, ends 140 of the flange 130 are relatively wide to provide extra protection and a support area on the sides of the holder 100 where the blood vessels are most likely to be placed. As shown in FIG. 14, the flange 130 may have flexible collar 142 to more securely attach the flange to the body 102 of a holder 100. The shape of the flange 130 during use may correspond to the anterior surface of the spine so that a snug fit against the spine is established during a spinal fusion procedure. The snug fit may help prevent tools used during the procedure from contacting and potentially damaging adjacent tissue. The flange 130 may be made of a semi-rigid elastic or plastic material so that an inner edge of the flange conforms to the shape of the holder body 102 after the flange has been stretched over and slid down the body. As shown in FIG. 14, the flange may have narrow brims 144, and relatively short ends 140. The ends 140 of the flange 130 are long enough to be easily positionable under adjacent vessels and tissue.

The distractors 114 and tangs 116 are protrusions, which may extend from the bottom of the holder body 102. Distractor 114 may serve to maintain distraction of adjacent vertebrae 54 during a spinal fusion procedure. The distractor 114 may establish a separation distance between the vertebrae during the procedure. Tangs 116 may also serve to maintain distraction. The tangs may maintain a parallel orientation of the vertebrae 54 during the procedure. Distractor 114 and tangs 116 may be substantially wedge-shaped to facilitate insertion into the disk space 44. Surfaces of distractor 114 and tangs 116 may be curved to match the curvature of the conduits 104, so that the distractor and tangs serve as partially enclosed extensions of conduits.

Figure 5:
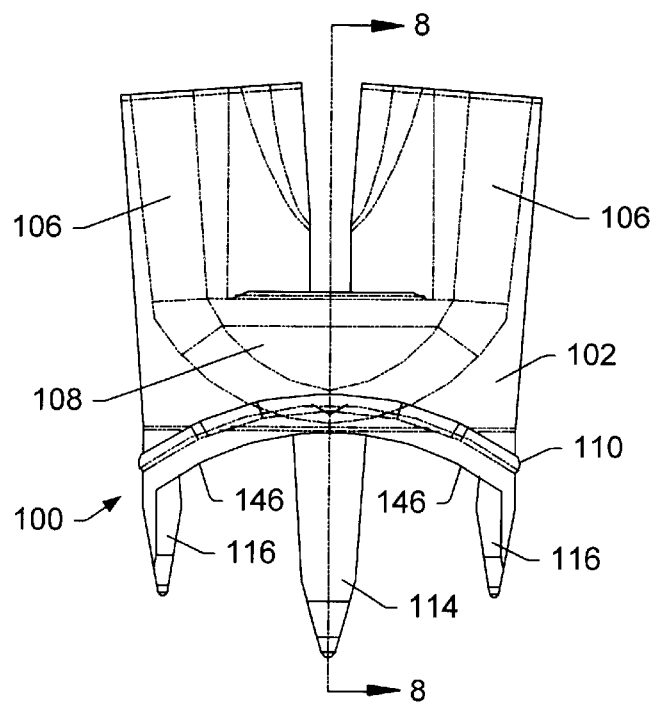
FIG. 5 is a front view the first embodiment holder.

Bottom 146 of the holder 100, as seen in FIG. 5, may conform to the general shape of a vertebra 54. When the holder is inserted into a disk space 44, portions of the bottom 146 of the holder 100 may reside on end caps 122 of adjacent vertebrae 54. Having the bottom 146 of the holder 100 shaped to conform to the shape of the vertebrae 54 may help to protect adjacent soft tissue and vessels from being pinched between the holder and the vertebrae during the spinal fusion procedure.

Figure 15:
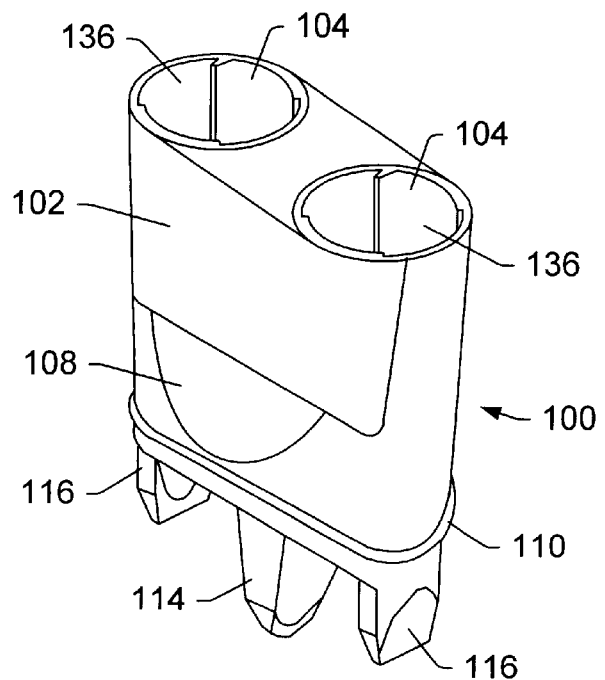
FIG. 15 is a perspective view of an embodiment of a holder without conduit extenders.
Figure 16:
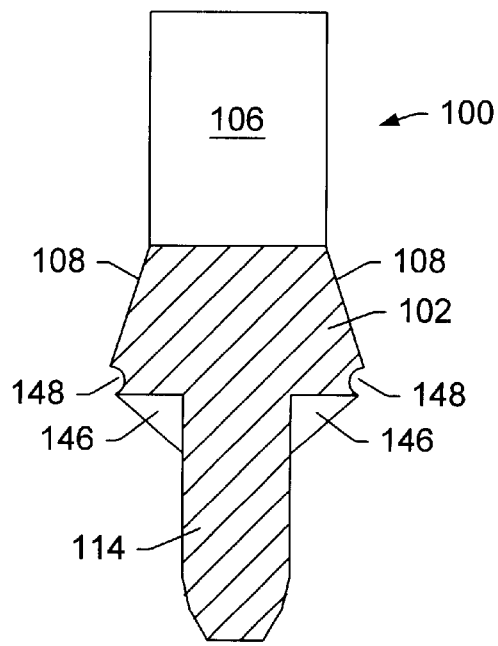
FIG. 16 is a cross sectional view of an embodiment of a holder having a flange groove.
Figure 17:
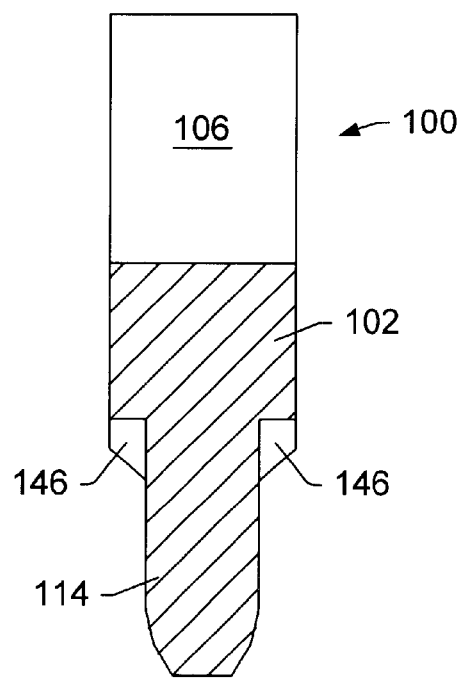
FIG. 17 is a cross sectional view of an embodiment of a holder without body flare.

FIGS. 15–21 show some alternate embodiments of a holder 100. FIG. 15 shows a holder without conduit extenders on the body 102. FIG. 16 shows a cross sectional view of a holder 100 with flange groove 148. The flange groove 148 may support an inner edge of a flange 130 to hold the flange at a desired position on the body 102. FIGS. 16 and 17 show cross sectional views of holders 100 without fastener holes. FIG. 17 also shows the holder without a flared portion and without a flange rim or a flange groove.

Figure 18:
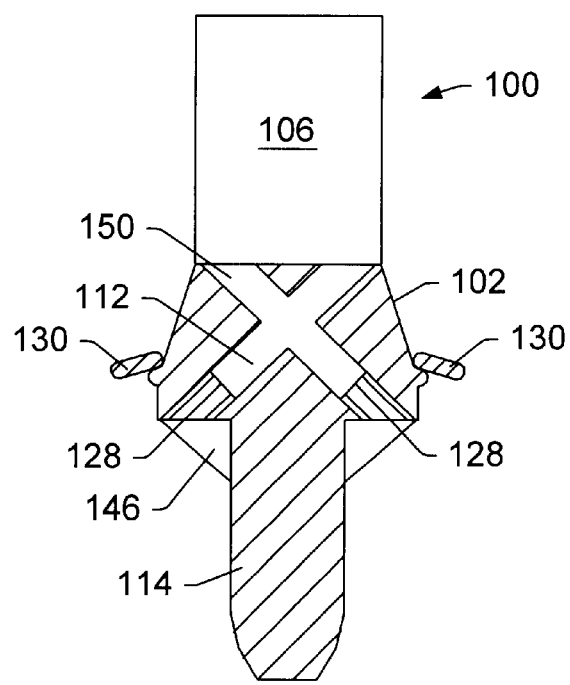
FIG. 18 is a cross sectional view of an embodiment of a holder with an alternative fastener hole arrangement.

FIG. 18 shows a cross sectional view of another embodiment holder with an alternate fastener hole 112 arrangement. In this embodiment, fastener holes 112 extend between conduits 104 from the top of body 102 downwards at an oblique angle relative to a vertical axis of holder 100. The fastener holes 112 cross at point 150 and then exit near an outer edge of the lower portion of body 102. The fastener holes 112 include shoulders 128 to limit the insertion depth of fasteners 120 into fastener holes 112. To use this embodiment, one fastener 120 is inserted into a fastener hole 112 and into a vertebra 54 until the head of the fastener is past the cross point 150. Then, another fastener 120 is inserted into the remaining fastener hole 112 and the fastener is inserted into the adjacent vertebra 54. Both fasteners 120 may be further inserted into the vertebrae 54 until the fastener heads contact the shoulders 128.

Figure 19:
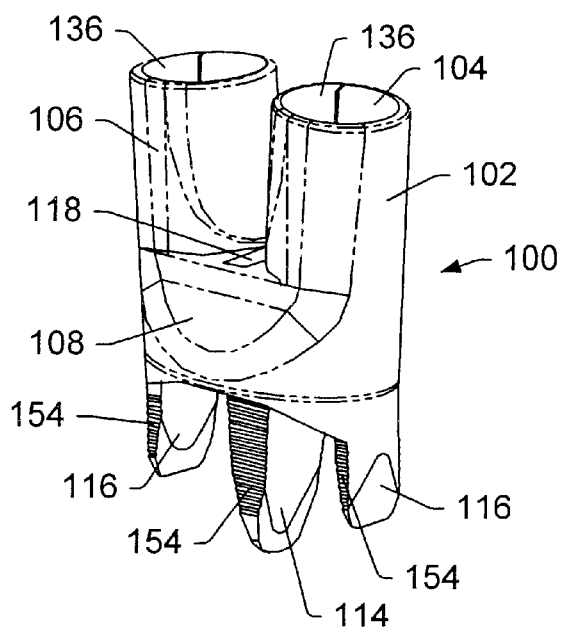
FIG. 19 is a perspective view of an embodiment of a holder having serrated distractors and tangs.

FIG. 19 shows an embodiment of a holder 100, which has serrations 154 on outer edges of the distractor 114 and on the outer edges of the tangs 116. Serrations 154 may maintain proper alignment and the serrations may inhibit the distractor 114 and tangs 116 from backing out of the vertebrae 54 after the holder 100 is inserted during a spinal fusion procedure.

Figure 20:
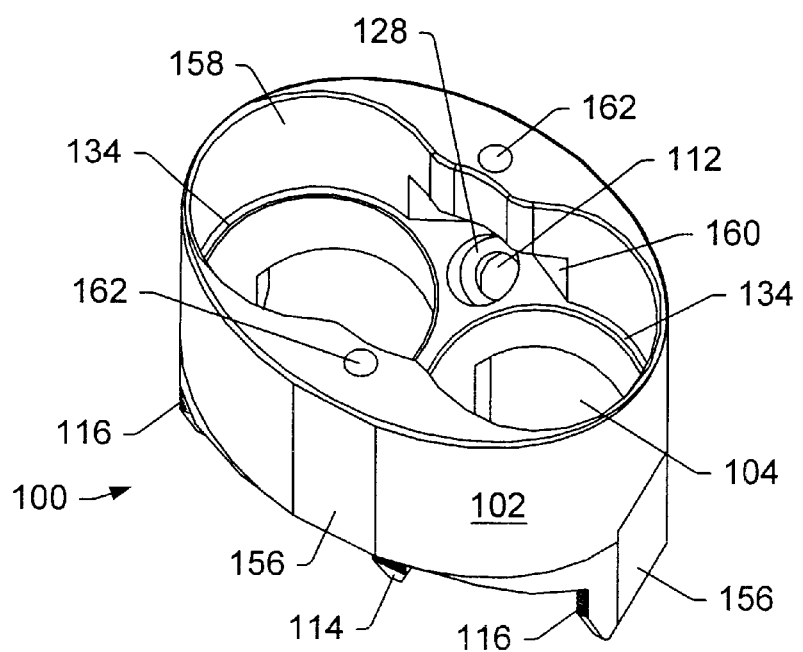
FIG. 20 is a perspective view of an embodiment of a holder having an extended upper opening and an insertion tool slot.
Figure 21:
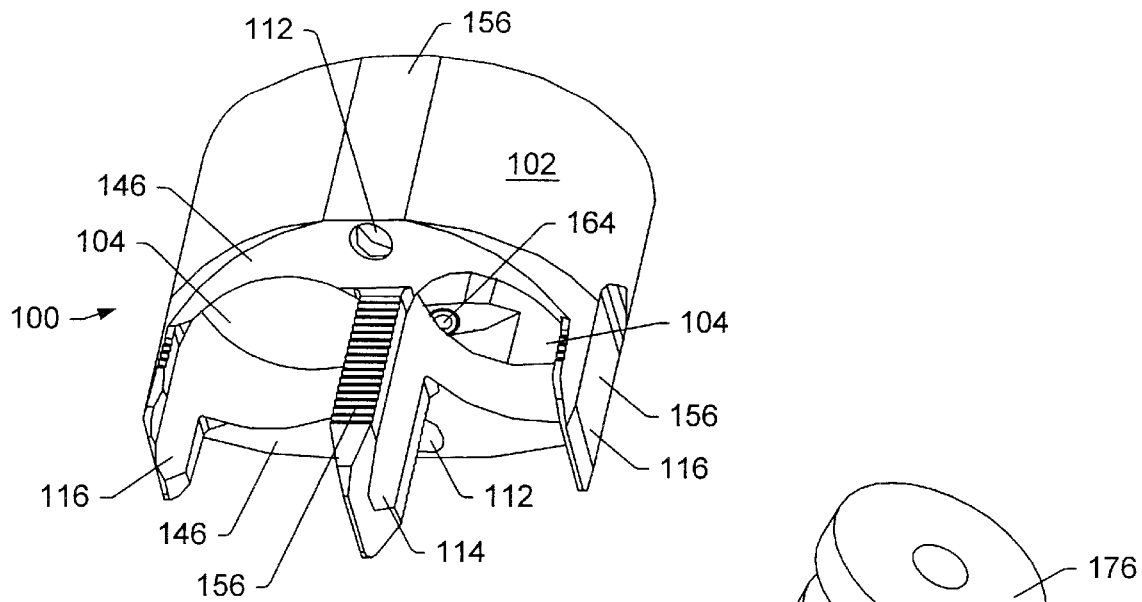
FIG. 21 is a perspective view of the embodiment shown in FIG. 20.

FIG. 20 and FIG. 21 show perspective views of an alternate embodiment of a holder 100. The body 102 may include flat sections 156, large top opening 158, undercut tool slots 160, spring stop 162, and ball 164. The flat sections 156 may help to make the holder 100 easier to machine during the manufacturing. The holder may have large top opening 158 with conduits 104 located in a lower section of the body. The body 102 may have undercut tool slots 160 (only one shown). Coil springs (not shown) are placed in the body 102 between the spring stops 162 and the balls 164 (only one shown). The spring stops 162, coil springs and balls 164 form an assembly that removably connects an insertion tool 166 to the holder 100.

Figure 22:
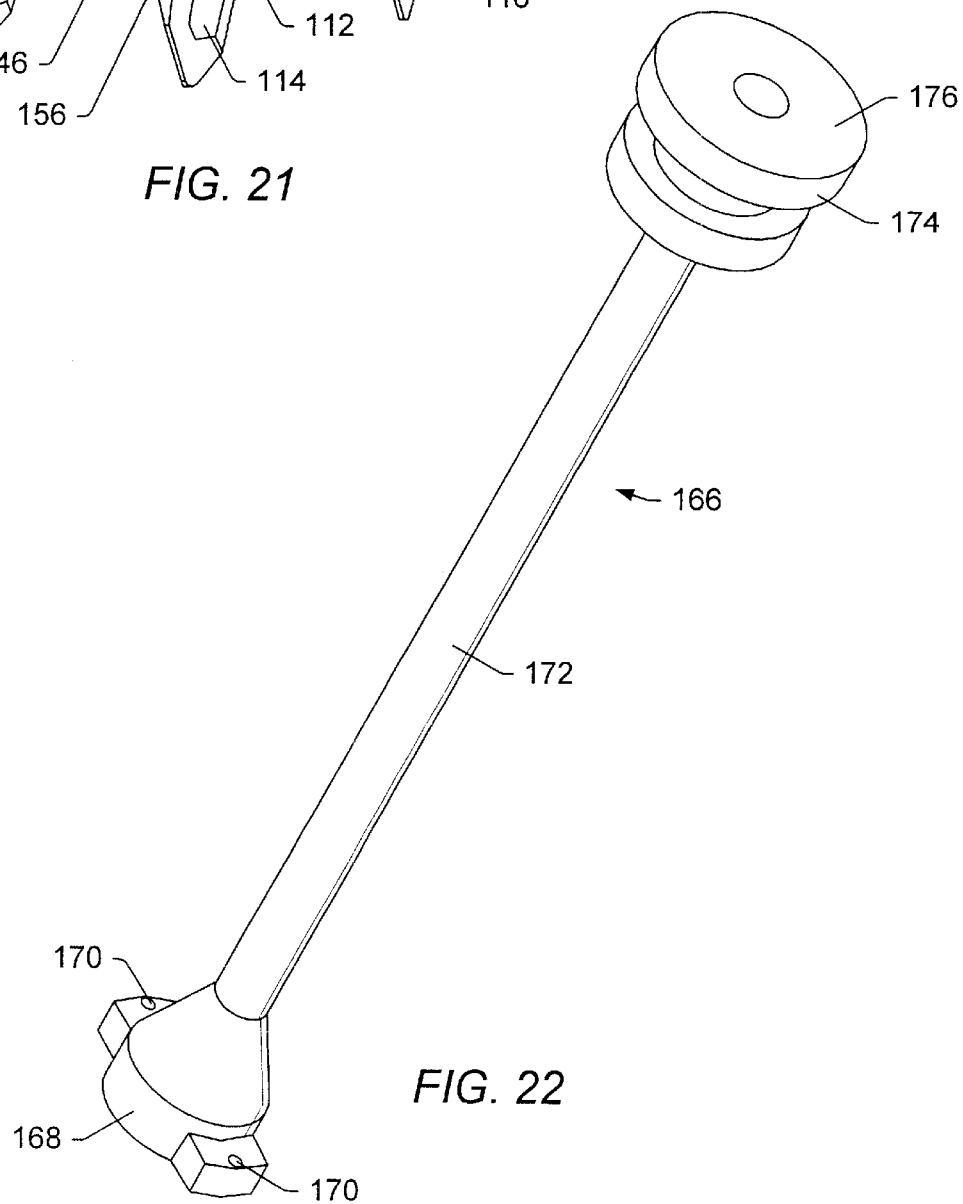
FIG. 22 is a perspective view of an insertion tool for an embodiment of a holder.

FIG. 22 shows a perspective view of the insertion tool 166 used with the holder shown in FIG. 20 and FIG. 21. The insertion tool 166 includes attachment head 168, dimples 170, shaft 172, and top member 174. The attachment head 168 of the insertion tool 166 is inserted into the top opening 158 of the body 102. The insertion tool 166 is rotated approximately 90 degrees. Rotating the insertion tool 166 forces the balls 164 in the holder body 102 against the coil springs, and compresses the springs. When the dimples 170 align with balls 164, the springs force the balls into the dimples and attach the insertion tool 166 to the holder 100. When the holder 100 is attached to the insertion tool 166, the insertion tool functions as a handle and allows the holder to be positioned at a desired location. A mallet (not shown) may be used to strike upper surface 176 of the top member 174 to insert the holder into a disk space 44 after the holder is positioned at a desired location. To remove the insertion tool 166 from the holder 100, the insertion tool is rotated approximately 90 degrees, and the attachment head 168 is removed from the opening 158.

Figure 23:
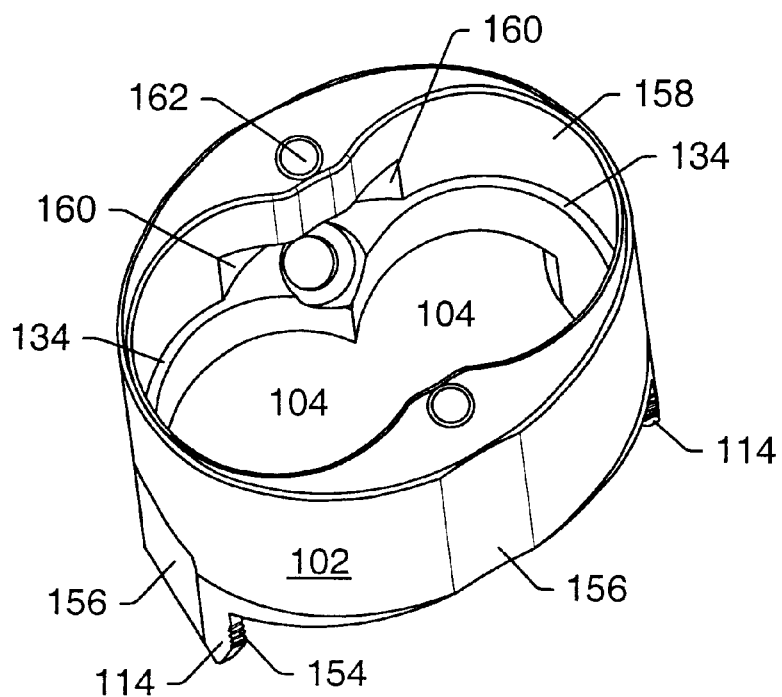
FIG. 23 is a perspective view of an alternate embodiment holder having overlapping conduits.
Figure 24:
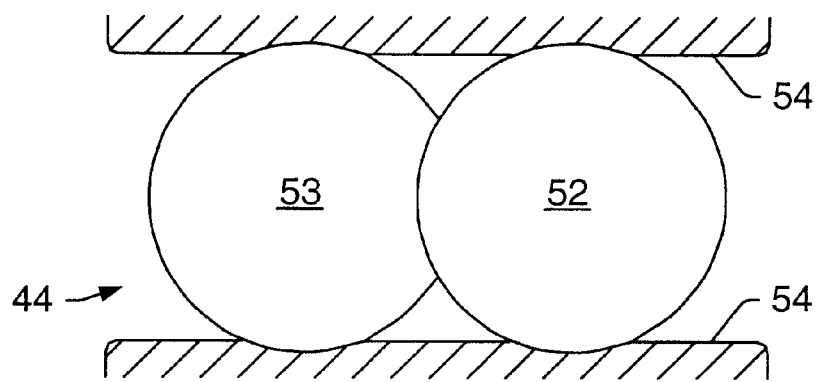
FIG. 24 is a top view of a possible arrangement of implants inserted into a disk space using the holder of FIG. 23.

FIG. 23 shows a perspective view of an embodiment of a holder 100 wherein the conduits 104 of the holder overlap. The holder has a pair of distractors 114 located at opposite sides of the body 102. FIG. 24 shows a schematic representation of one possible arrangement of implants 52, 53 inserted in a disk space 44 with the embodiment of a holder 100 shown in FIG. 23.

Figure 25:
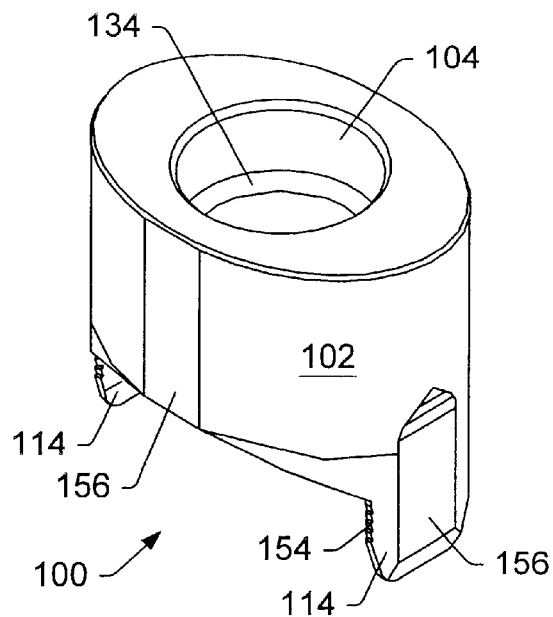
FIG. 25 is a perspective view of a holder having one conduit.

FIG. 25 shows an embodiment of the holder 100 having one conduit 104 extending through the body 102. The holder 100 may have a pair of distractors 114 located at opposite sides of the conduit 104. The holder may have fastener holes (not shown) that allow fasteners to attach the holder to vertebrae 54 during a spinal fusion procedure.

Figure 26:
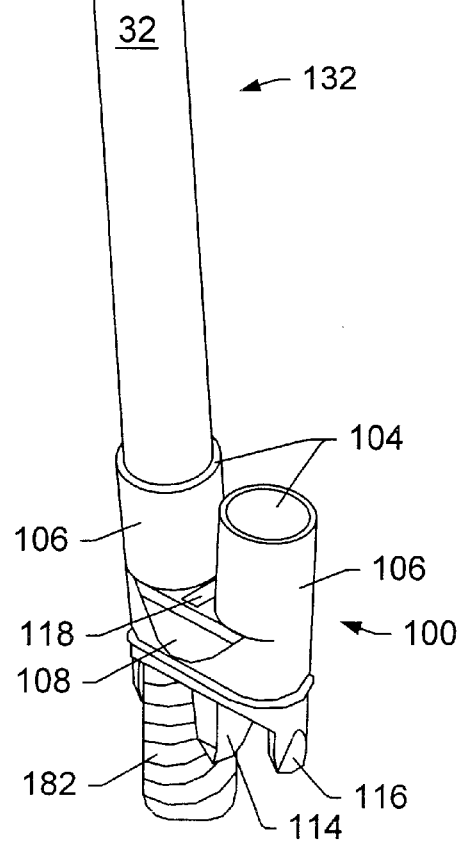
FIG. 26 is a perspective view of a holder with an inserted protective sleeve and tool.

FIG. 26 illustrates an embodiment of a holder 100 with protective sleeve 132, driver 180, and attachment 182. Tube 32 of protective sleeve 132 may be inserted in one of the conduits 104 of holder 100. Shaft 184 of driver 180 may be inserted in tube 32. At least a portion of shaft 184 may have a diameter substantially equal to the inside diameter of tube 32 to maintain alignment of the driver 180 during use. Stop 186 may serve to limit the distance shaft 184 may be inserted into tube 32. In some embodiments, stop 186 may be adjustable to allow different insertion depths. The driver 180 may have handle 188 for turning shaft 184 located on an end of the shaft. Attachment 182 may be located on an end of the shaft opposite to the handle 188. Attachments may include, but are not limited to, drilling heads and tapping heads. An implant 52 may also be coupled to the distal end of a driver for insertion into a disk space 44.

Figure 27:
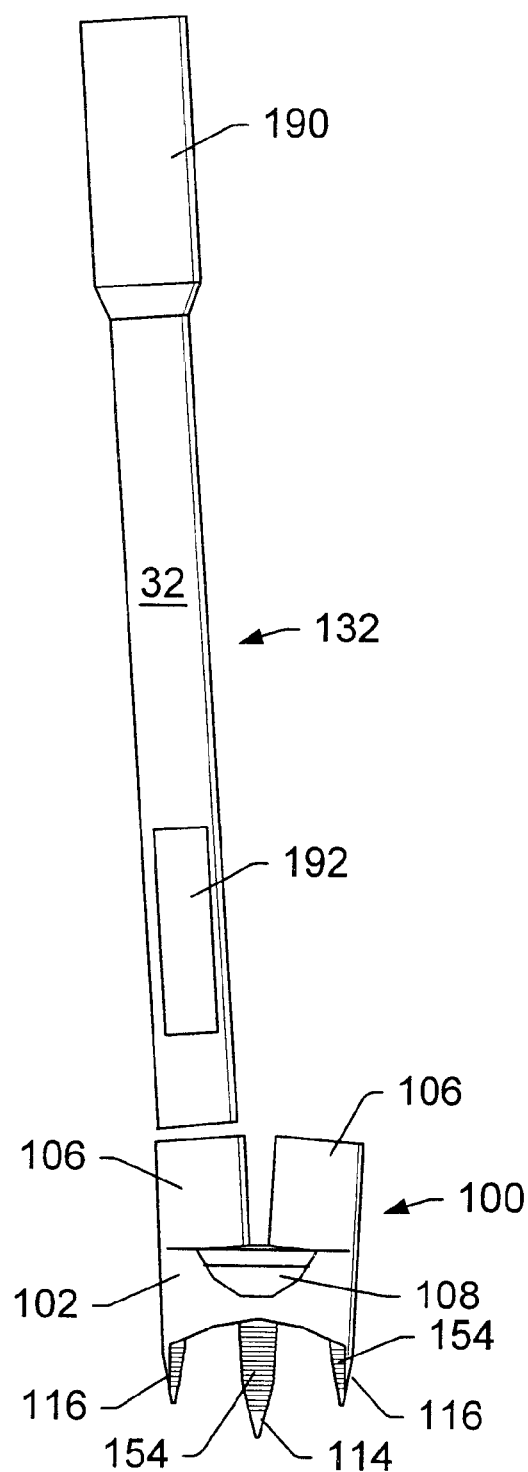
FIG. 27 is a front view of a holder with an alternate protective sleeve.

FIG. 27 illustrates an embodiment of a protective sleeve 132 prior to insertion into an embodiment of a holder 100. The protective sleeve 132 includes widened portion 190 at an end of the sleeve. The widened portion 190 receives a tool (not shown) having a complementary wide portion at an end of the tool. The sleeve 132 may include view-port 192 to provide improved visibility of the surgical site during the procedure. The view-port may be a window, a slot, or other structure that allows increased visibility of the surgical site during the procedure.

FIGS. 28a–28e illustrate steps included in a spinal fusion procedure using an embodiment of a holder 100. In FIG. 28a, holder 100 is shown being inserted into disk space 44 between adjacent vertebrae 54. Distractor 114 may be driven into the disk space 44 by striking insertion device 194 with mallet 196. Insertion device 194 may fit in the conduits 104. Alternately, insertion device 194 may fit between conduits 104 in slot 118 to provide a contact surface with the holder 100 for hammering. In the embodiments of the holder 100 shown in FIGS. 20, 21, and 23, the insertion device may be an insertion tool 166 as shown in FIG. 22. The insertion device 194 may be coupled with holder 100 prior to insertion into the surgical cavity, and may be used as a handle for inserting and positioning holder 100 by the surgeon prior to and during hammering. Distractor 114 separates vertebrae 54 as the distractor is hammered in. The distractor widens the disk space 44 to the desired width for the procedure. Holder 100 may be hammered with the mallet 196 until the bottom 146 of body 102 makes substantial contact with the adjacent vertebra 54.

Figure 29:
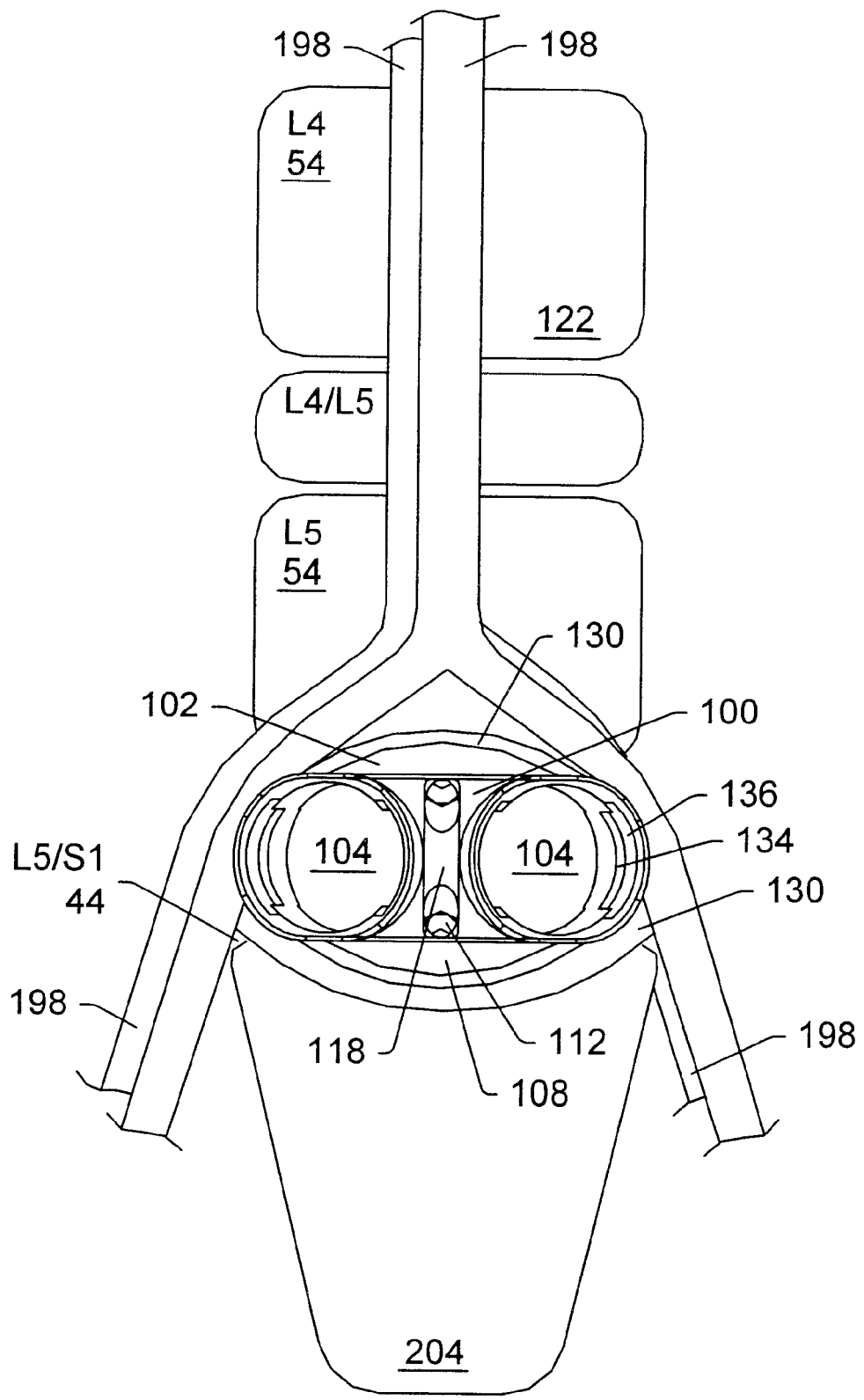
FIG. 29 illustrates the positioning of major blood vessels around one embodiment of a holder during a typical L5/S1 fusion procedure.
Figure 30:
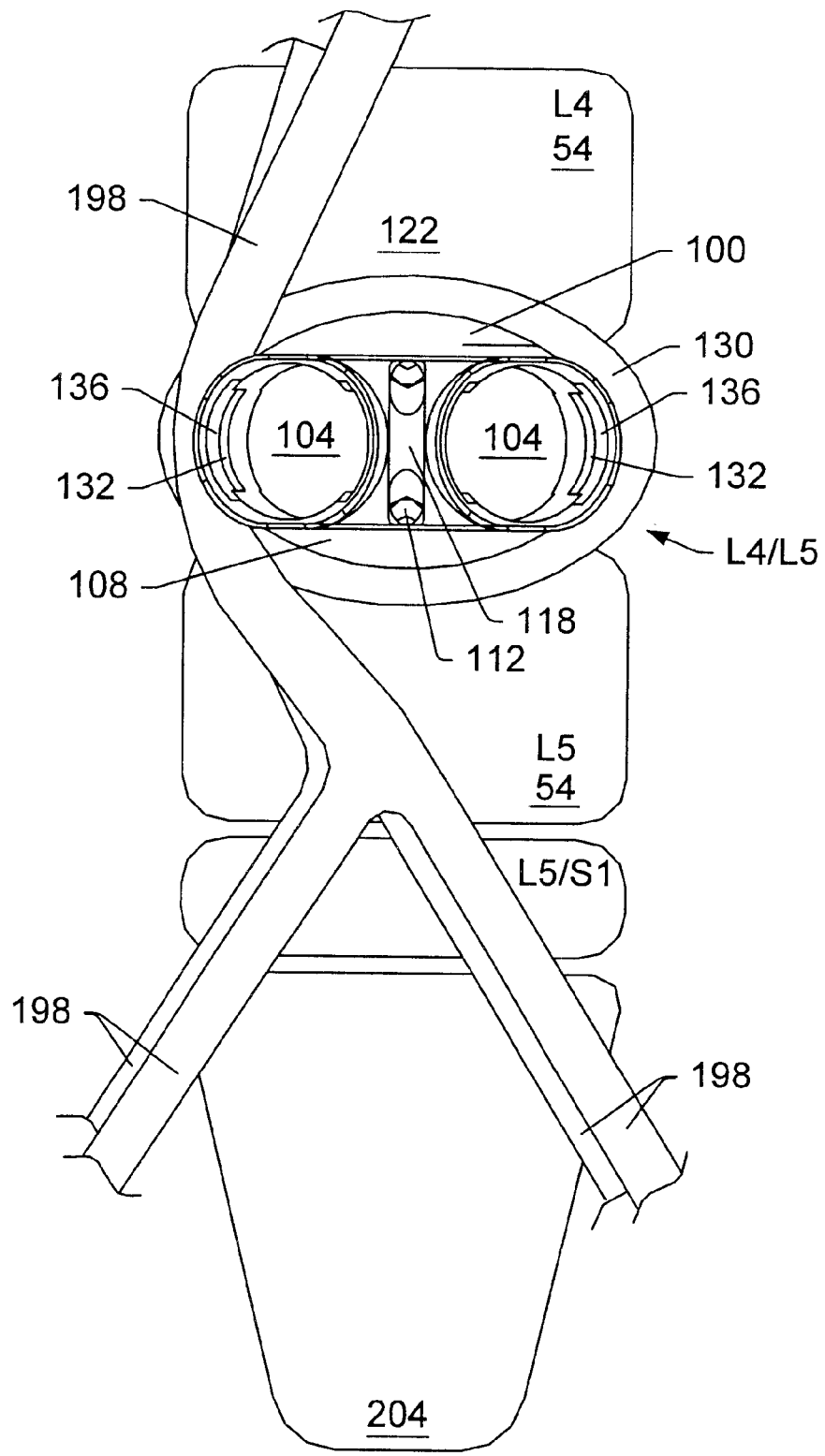
FIG. 30 illustrates the positioning of major blood vessels around one embodiment of a holder during a typical L4/L5 fusion procedure.

In FIG. 28b, holder 100 has been hammered into the disk space 44 to an optimal depth. Optional flange 130 may then be slipped over the top of holder 100 to fit snugly against flange rim 110. After flange 130 is installed, blood vessels 198, such as the aorta and vena cava, which are retracted to one side during the installation of the holder 100, may be placed over flange 130 next to body 102, as shown in FIG. 29 and FIG. 30. The shape of flange 130 serves to protect the blood vessels 198 from being pinched, nicked or cut during the remainder of the spinal fusion procedure. Body 102 may be formed with smooth, arcuate outer surfaces with no sharp corners to further protect blood vessels 198 and tissue.

FIG. 28c shows the insertion of optional fasteners 120 in fastener holes 112, through end caps 122 and into cancellous bone 124 of vertebrae 54. Angling of fasteners 120 into cancellous bone 124 avoids vertical penetration deep into the end plates 126; thus helping to prevent weakening of the endplates near the implants 52. The head of driver 200 may fit into slot 118 to contact a fastener 120. The slot 118 may protect surrounding soft tissues should the head of the driver 200 slip off the fastener 120. Slot 118 may also help contain a fastener 120 should the fastener be dropped during the insertion process. In some embodiments, the heads of fasteners 120 may include hex or star shaped slots for receiving a corresponding driver 200. In some embodiments, driver 200 may include a bent or bendable shaft to facilitate the angled insertion of the fasteners 120 in the fastener holes 112. In some embodiments, the shaft of driver 200 may be long enough to allow the surgeon to turn the driver above the surgical cavity while the head of the driver is coupled to the head of a fastener 120. In some embodiments, a fastener 120 may be coupled to the driving head of driver 200 to help prevent dropping the fastener into the surgical cavity during insertion.

In FIG. 28d, protective sleeve 132 is inserted in one of the conduits 104 of the holder 100. Shaft 184 of driver 180 is inserted into the protective sleeve 132. Stop 186 serves to limit the distance shaft 184 may be inserted into sleeve 132. Drilling head 182 may be coupled to the distal end of driver 180. A handle (not shown) coupled to the proximal end of driving shaft 184 may be turned while applying downward pressure on driver 180 to drill out a hole in disk space 44. Drilling the hole may also remove bone from the end plates 126 of adjacent vertebrae 54. Flange 130 may protect adjacent blood vessels 198 and other soft tissues during the drilling process.

In spinal fusion procedures using threaded implants, after the hole is drilled, driver 180 is retracted and a tap (not shown) is attached to the driver. The tap and the driver 180 are inserted into the sleeve 132. A handle (not shown) coupled to an end of the driving shaft 184 is turned while applying downward pressure on driver 180 to tap a flight of threads in the vertebrae 54. After a flight of threads is formed in the hole, the driver is removed from the protective sleeve 132.

Referring to FIG. 28e, a threaded implant 52 is coupled to the distal end of an implant insertion tool 202. The implant insertion tool 202 is inserted into the sleeve 132. A handle (not shown) coupled to the proximal end of implant insertion tool 132 is turned while applying downward pressure to screw implant 52 into the threaded hole in disk space 44.

In spinal fusion procedures using unthreaded implants, after the hole is drilled, an unthreaded implant 52 is coupled to an end of an implant insertion tool 202. The implant insertion tool 202 is inserted into the protective sleeve 132. A mallet (not shown) is used to strike the proximal end of implant insertion tool 202 to drive implant 52 into the disk space 44.

In all embodiments, inserted implant 52 is then detached from insertion tool 202. Protective sleeve 132 may then be removed from the conduit 104 of holder 100 and inserted into the adjacent holder conduit 104. Optionally, a second protective sleeve 132 may be inserted in the adjacent conduit 104. The steps described for FIGS. 28d–28e may then be repeated for the installation of the second implant. After the second implant 52 is installed, fasteners 120 may be backed out of vertebrae 54 and holder 100 may be removed from the disk space 44.

An advantage of holder 100 illustrated in FIGS. 28a–28e is that the tools and protective sleeve 132 may be removed at any time during the procedure without affecting the alignment or spacing of the holder 100. Fixing the holder 100 to the vertebrae with fasteners 120, and inserting the protective sleeve 132 into the holder 100 only when necessary may minimize the risk of misalignment of implants 52 during a spinal fusion procedure.

FIG. 29 illustrates the positioning of major blood vessels 198 around a dual-conduit holder 100 during an L5/S1 fusion procedure. Holder 100 is shown inserted in disk space 44 (L5/S1) between vertebra 54 (L5) and sacrum 204 (S1). The bifurcation of major blood vessels 198 (the aorta and vena cava) typically is proximate vertebra L5. The right branch and left branch of major blood vessels 198 are shown separated and placed over holder flange 130. In some patients, the bifurcation point of the major blood vessels 198 may be located higher or lower than proximate the L5 vertebra. An irregularly located bifurcation point of the major blood vessels 198 may require the branches of the major blood vessels to be routed around one side of holder 100.

FIG. 30 illustrates the positioning of major blood vessels 198 around a holder 100 during an L4/L5 fusion process. Holder 100 is shown inserted in disk space 44 (L4/L5) between adjacent vertebrae 54 (L4 and L5). The bifurcation of major blood vessels 198 typically is proximate vertebra L5. The major blood vessels 198 are shown placed over holder 100 upon flange 130. The blood vessels may be placed on either side of holder 100.

The configuration of holder 100 and the added protection of flexible flange 130 may serve to protect the blood vessels 198 from being nicked during the spinal fusion procedure. In addition, the body 102 of holder 100 may be curved and may lack sharp corners or edges to further protect the blood vessels 198 and other tissue from abrasion. Protecting the blood vessels 198 is critical in a spinal fusion procedure, as the aorta is a major artery and the vena cava is a major vein. Even a tiny nick in either blood vessel 198 is potentially catastrophic, and must be repaired quickly. A nick in the vena cava is particularly problematic because the vena cava has thinner walls than the aorta, making the vena cava easier to nick and harder to repair than the aorta.

Figure 3:
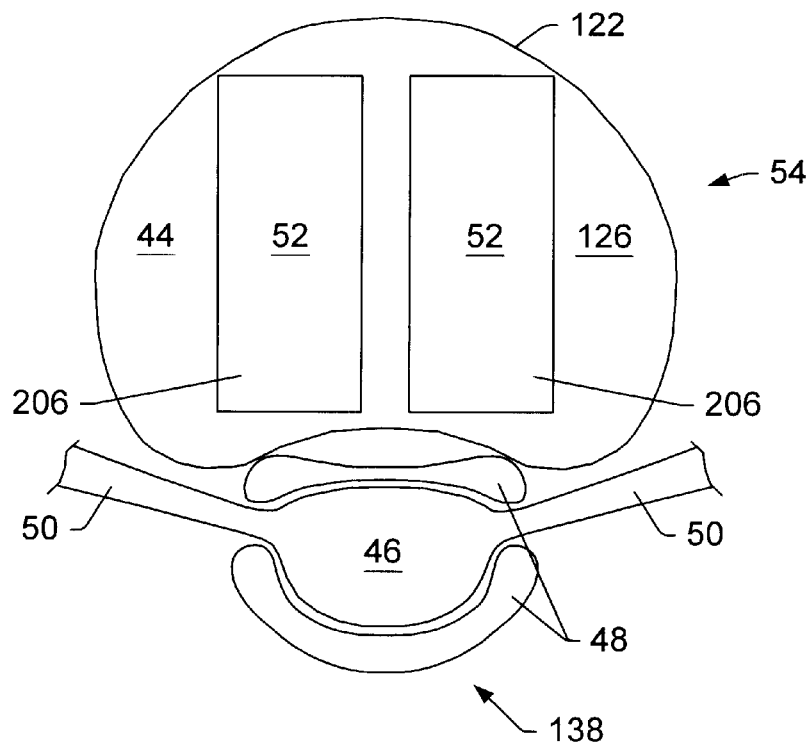
FIG. 3 is a representation of implants inserted into a disk space with a dual-tube protective sleeve, or with an embodiment of a holder of the present invention that has parallel conduits.
Figure 4:
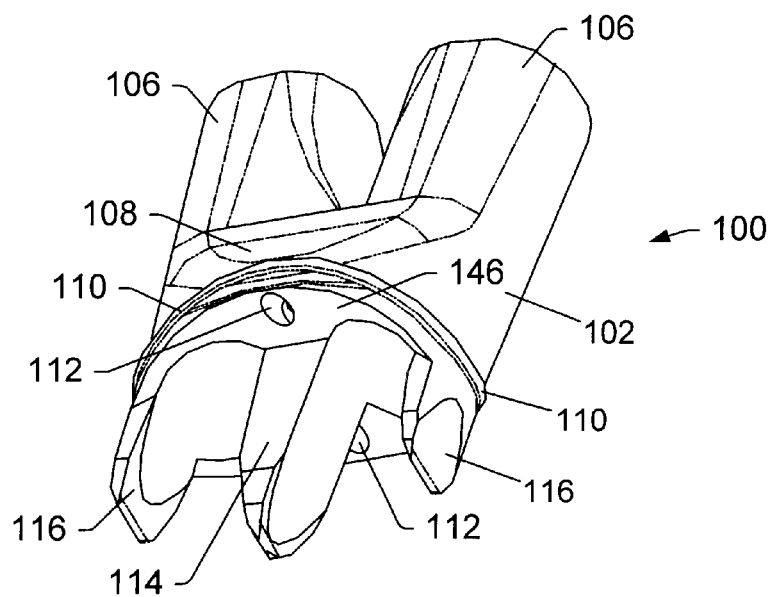
FIG. 4 is a perspective view of a first embodiment of a holder.

FIG. 3 illustrates the orientation of implants 52 inserted using dual-tube protective sleeves 40 or an embodiment of holder 100 that has an angle A value of 0 degrees. Implants 52 are shown inserted in parallel in disk space 44. Spinal nerves within the spinal canal 46 and protective sheath 48 (also called the dura) are shown posterior to disk space 44. Nerves 50 exit the sides of spinal canal 46. An end 206 of an implant 52 may put pressure on nerves 50 if the implant is inserted far enough to allow ends to protrude out the posterior side 138 of disk space 44. Pressure on the nerves may lead to severe post-operative pain or nerve damage for the patient.

Figure 31:
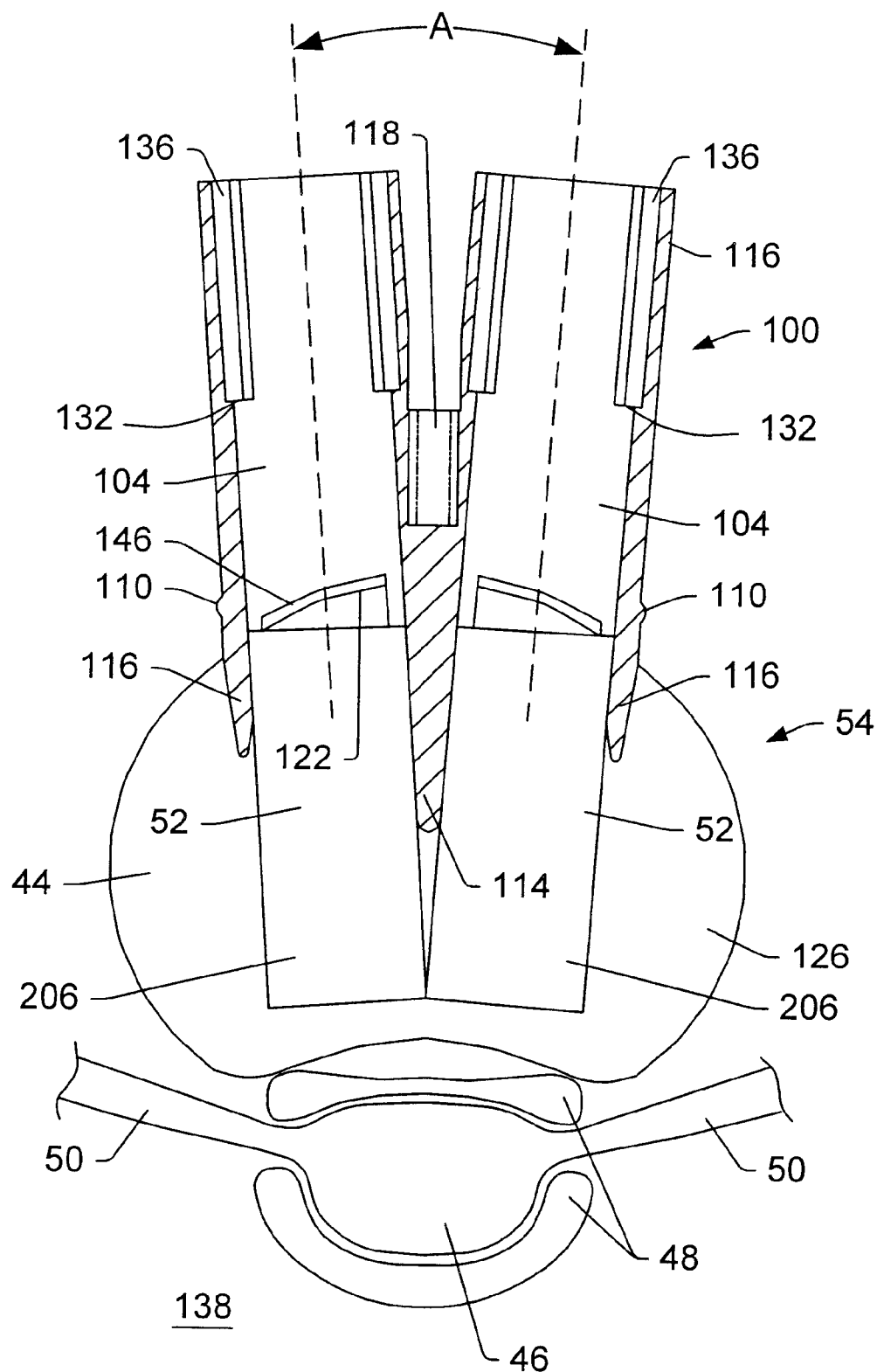
FIG. 31 illustrates the angulation of implants inserted using one embodiment of a holder.

FIG. 31 illustrates the angulation of implants inserted using one embodiment of a holder 100. Implants 52 are shown inserted angled inwards in disk space 44. Nerves 50 are shown exiting from the sides of spinal canal 46. If implants 52 are inserted far enough that ends 206 protrude out the posterior side 138 of the disk space 44, ends 206 may be more likely to put pressure on dura 48 than on nerves 50. Dura 48 may be less likely to be negatively affected by the pressure than nerves 50.

Also shown in FIG. 31 is an embodiment of a holder 100 inserted in disk space 44. The curvature of bottom 146 of holder 100 may substantially match the curvature of the anterior surface of the adjacent vertebrae 54. The close fit between the vertebrae 54 and the holder 100 may help protect blood vessels 198 and other soft tissues from being pinched between the vertebrae and the holder during the spinal fusion procedure. The angulation of conduits 104 is shown as angle A. Different embodiments of holder 100 may be made with a wide range of angles A to be used in spinal fusion procedures requiring different optimal angulations of implants 52. Most procedures may fall between 0 degrees and 30 degrees. Approximately 8 degrees may be the optimal angulation for implants 52 in many procedures.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A base for use during a spinal fusion procedure, comprising:
    a body;
    a first hole in the body, the hole configured to receive a fastener that couples the body to a first vertebra during use; and
    a conduit through the body;
    wherein the conduit is configured to allow tools or devices for implanting a spinal fusion device, or for preparing a patient to receive a spinal fusion device, to be inserted in a disk space adjacent to the first vertebra.

2. The base as defined in claim 1, further comprising a second hole in the body, the second hole configured to receive a fastener that couples the body to a second vertebra during use.

3. The base as defined in claim 1, further comprising a sleeve, and wherein an end of the sleeve is removably positionable in the conduit.

4. The base as defined in claim 3, further comprising a shoulder in the conduit, the shoulder configured to limit insertion depth of the sleeve into the conduit.

5. The base as defined in claim 3, further comprising a slot in a conduit wall, the slot configured to engage a distractor on an end of the sleeve during use.

6. The base as defined in claim 3, wherein the sleeve further comprises a view-port to provide increased visibility of a surgical site during use.

7. The base as defined in claim 1, further comprising a protrusion extending from the body, the protrusion configured to be positionable within the disk space during use.

8. The base as defined in claim 7, wherein the protrusion establishes a separation distance between the first vertebra and a second vertebra during use.

9. The base as defined in claim 7, wherein the protrusion comprises sides and further comprising serrations on at least one side of the protrusion.

10. The base as defined in claim 1, further comprising a flange, the flange having an inner edge, an outer edge, a lower surface and an upper surface, wherein the flange is positionable around the body, and wherein the flange is configured to protect tissue and vessels adjacent to the disk space during use.

11. The base as defined in claim 10, wherein the flange is made of a semi-rigid material.

12. The base as defined in claim 10, wherein the lower surface of the flange curves during use to substantially match curvatures of vertebrae adjacent to the holder.

13. The base as defined in claim 10, further comprising a rim on a portion of an outer surface of the body, wherein the rim engages the lower surface of the flange to support the flange during use.

14. The base as defined in claim 10, further comprising a groove on a portion of an outer surface of the body, wherein the groove engages the inner edge of the flange to support the flange during use.

15. The base as defined in claim 10, wherein the flange further comprises an elastic collar which conforms to the shape of the body during use to support and secure the flange against the body.

16. The base as defined in claim 1, wherein a height of the body is less than about six inches.

17. The base as defined in claim 1, wherein a height of the body is less than about four inches.

18. The base as defined in claim 1, wherein a height of the body is less than about two inches.

19. The base as defined in claim 1, wherein the first hole passes through the body at an oblique angle relative to a vertical axis of the body.

20. The base as defined in claim 1, wherein the bottom of the body is curved to substantially conform to curvatures of vertebrae adjacent to the holder during use.

21. The base as defined in claim 1, wherein portions of the body contact vertebral end caps during use.

22. The base as defined in claim 1, wherein the base comprises a smooth outer surface.

23. The base as defined in claim 7, wherein an end of the protrusion has a wedge shape.

24. The base as defined in claim 7, wherein a surface of the protrusion is an extension of a portion of an inner surface of the conduit.

25. The base as defined in claim 7, wherein the protrusion is configured to inhibit rotation of the body when positioned within the disk space during use.

26. The base as defined in claim 7, wherein the protrusion establishes a separation distance so that the first vertebra is substantially parallel to a second vertebra.

27. The base as defined in claim 1, wherein the conduit passes through the body at an oblique angle relative to a vertical axis of the body.

28. The base as defined in claim 1, wherein the conduit passes through the body substantially parallel to a vertical axis of the body.

29. The base as defined in claim 1, wherein the conduit comprises a shoulder to limit insertion depth of tools or devices therein.

30. A base for use during a spinal fusion procedure, comprising:
    a body;
    a first conduit through the body;
    a second conduit through the body; and
    a first hole in the body, the hole configured to receive a fastener that couples the body to a first vertebra during use;
    wherein tools or devices inserted into the first conduit or the second conduit during use are positionable in a disk space adjacent to the first vertebra.

31. The base as defined in claim 30, further comprising a second hole in the body, the second hole configured to receive a fastener that couples the body to a second vertebra during use.

32. The base as defined in claim 30, further comprising a sleeve, and wherein an end of the sleeve is removably positionable in the first conduit or the second conduit during use.

33. The base as defined in claim 32, wherein the sleeve further comprises a view-port to provide increased visibility of a surgical site during use.

34. The base as defined in claim 32, further comprising a shoulder in the first conduit, wherein the shoulder limits insertion depth of the sleeve into the first conduit.

35. The base as defined in claim 32, wherein the first conduit further comprises a slot on an inner surface, the slot configured to engage a distractor on an end of the sleeve during use.

36. The base as defined in claim 30, wherein the bottom of the body is curved to substantially conform to curvatures of vertebrae adjacent to the holder during use.

37. The base as defined in claim 30, further comprising a flange, the flange having an inner edge, an outer edge, a lower surface, and an upper surface, wherein the flange is positionable around the body, and wherein the flange is configured to protect tissue and vessels adjacent to the disk space during use.

38. The base as defined in claim 37, wherein the flange is made of a semi-rigid material.

39. The base as defined in claim 37, wherein a lower surface of the flange curves during use to substantially match curvatures of surfaces of vertebrae adjacent to the holder.

40. The base as defined in claim 37, wherein the flange further comprises an elastic collar configured to conform to the shape of the body during use to support the flange.

41. The base as defined in claim 37, further comprising a rim on a portion of an outer surface of the body, wherein the rim is configured to engage the lower surface the flange during use.

42. The base as defined in claim 37, further comprising a groove on a portion of an outer surface of the body, wherein the groove is configured to engage the inner edge of the flange during use.

43. The base as defined in claim 30, wherein the first and second conduits are substantially parallel.

44. The base as defined in claim 30, wherein the conduits are angled relative to each other.

45. The base as defined in claim 44, wherein a distance between a centerline of the first conduit and a centerline of the second conduit at a top of the body is greater than a distance between centerlines of the conduits at the bottom of the body.

46. The base as defined in claim 45, wherein an angle between the centerlines of the conduits is less than about 30 degrees.

47. The base as defined in claim 45, wherein an angle between the centerlines of the conduits is less than about 20 degrees.

48. The base as defined in claim 45, wherein an angle between the centerlines of the conduits is between about 2 degrees and about 10 degrees.

49. The base as defined in claim 45, wherein the body further comprises two sides, and wherein the sides flare such that a largest width of the body measured from side to side is proximate the bottom of the body.

50. The base as defined in claim 31, wherein the first hole and the second hole are obliquely angled through the body relative to a vertical axis of the body.

51. The base as defined in claim 31, wherein the body further comprises:
    a first side and a second side; and
    wherein the holes are located between the first and second conduits;
    wherein an entry of the first hole is located on a top of the body proximate the first side, and an exit of the first hole is located on a bottom of the body proximate the second side; and
    wherein an entry of the second hole is located on the top of the body proximate the second side, and an exit for the second hole is located on the bottom of the body proximate the first side.

52. The base as defined in claim 31, wherein the body further comprises:
    a first side and a second side;
    an opening in a top portion of the body, the opening defined by a lower surface;
    wherein an entry of the first hole is located in the lower surface of the opening near the first side, and an exit of the first hole is located on a bottom of the body proximate the first side; and
    wherein an entry for the second hole is located in the lower surface of the opening near the second side, and an exit for the second hole is located on the bottom of the body proximate the second side.

53. The base as defined in claim 52, wherein the opening is located between the first conduit and the second conduit.

54. The base as defined in claim 30, wherein a height of the body is less than about six inches.

55. The base as defined in claim 30, wherein a height of the body is less than about four inches.

56. The base as defined in claim 30, wherein a height of the body is less than about two inches.

57. The base as defined in claim 30, wherein a portion of the first conduit overlaps a portion of the second conduit.

58. The base as defined in claim 30, wherein the body comprises a smooth outer surface.

59. The base as defined in claim 30, wherein the first hole comprises a shoulder to limit insertion depth of the fastener.

60. The base as defined in claim 44, wherein the distance between a centerline of the first conduit and a centerline of the second conduit at a top of the body is less than a distance between the centerlines of the conduits at a bottom of the body.

61. A base for use during a spinal fusion procedure, comprising:
    a body having a height of less than about six inches, the body comprising a conduit through the body;
    at least one protrusion extending from the body, wherein the at least one protrusion comprises serrations on at least one side of the at least one protrusion; and
    wherein the conduit is configured to allow tools or devices for implanting a spinal fusion device, or for preparing a patient to receive a spinal fusion device, to be inserted in a disk space through the conduit.

62. The base of claim 61, wherein portions of the body contact vertebral end caps during use.

63. The base of claim 61, wherein the body comprises a smooth outer surface.

64. The base of claim 61, wherein a centerline of the conduit is substantially parallel to a vertical axis of the body.

65. The base of claim 61, wherein a centerline of the conduit is angled oblique to a vertical axis of the body.

66. The base of claim 61, further comprising a shoulder in the conduit, wherein the shoulder is configured to limit insertion depth of tools or devices for implanting into the conduit.

67. The base of claim 61, further comprising a flange removably coupled to the body, wherein the flange protects tissue and vessels adjacent to the base during use.

68. The base of claim 67, wherein the flange is made of a semi-rigid material.

69. The base of claim 67, wherein the flange comprises a collar configured to conform to the body to support the flange during use.

70. The base of claim 67, wherein a lower surface of the flange curves to substantially match surface curvatures of vertebrae located adjacent to the base during use.

71. The base of claim 61, wherein the body further comprises a bottom having a curvature configured to substantially conform to curvatures of vertebrae adjacent to the base during use.

72. The base of claim 61, wherein the at least one protrusion is configured to establish a substantially parallel spacing between adjacent vertebrae when positioned within the disk space during use.

73. The base of claim 61, wherein the at least one protrusion is configured to inhibit rotation of the base when the at least one protrusion is positioned within the disk space during use.

74. The base of claim 72, wherein an end of the at least one protrusion has a wedge shape.

75. A base for use during a spinal fusion procedure, comprising:
   a body having a height of less than about six inches, said body comprising a conduit through the body;
   a flange, the flange having an inner edge, an outer edge, a lower surface and an upper surface, wherein the flange is positionable around the body, wherein a portion of the flange comprises elastic material that holds the flange to the body, and wherein the flange is configured to protect tissue and vessels adjacent to a disk space during use;
   at least one protrusion extending from the body; and
   wherein the conduit is configured to allow tools or devices for implanting a spinal fusion device, or for preparing a patient to receive a spinal fusion device, to be inserted in the disk space through the conduit.

76. The base as defined in claim 75, wherein the body further comprises a bottom having a surface configured to substantially conform to surfaces of vertebrae adjacent to the base during use.

77. The base of claim 75, wherein portions of the body contact vertebral end caps during use.

78. The base of claim 75, wherein the body comprises a smooth outer surface.

79. The base of claim 75, wherein a centerline of the conduit is parallel to a vertical axis of the body.

80. The base of claim 75, wherein a centerline of the conduit is angled oblique to a vertical axis of the body.

81. The base of claim 75, wherein the at least one protrusion is configured to establish a substantially parallel spacing between adjacent vertebrae when positioned within the disk space during use.

82. The base of claim 75, wherein the at least one protrusion is configured to inhibit rotation of the base when the at least one protrusion is positioned within the disk space during use.

83. The base of claim 75, wherein an end of the at least one protrusion has a wedge shape.

84. The base of claim 75, wherein the flange is made of a semi-rigid material.

85. The base as defined in claim 75, wherein the flange comprises a collar configured to conform to the body to support the flange during use.

86. The base as defined in claim 75, wherein the lower surface of the flange curves to substantially match surface curvatures of vertebrae located adjacent to the base during use.

87. The base as defined in claim 75, further comprising a rim on a portion of an outer surface of the body, wherein the rim is configured to engage the flange to support the flange on the body during use.

88. The base as defined in claim 75, further comprising a groove on a portion of an outer surface of the body, wherein the groove is configured to engage the inner edge of the flange to support the flange during use.

89. The base as defined in claim 75, wherein the flange further comprises a collar configured to conform to the body to support the flange during use.

90. A base for use during a spinal fusion procedure, comprising:
   a body having a height of less than about six inches, wherein a bottom of the body is curved to substantially conform to curvatures of vertebrae adjacent to the base during use;
   a conduit through the body;
   at least one protrusion extending from the body; and
   wherein the conduit is configured to allow tools or devices for implanting a spinal fusion device, or for preparing a patient to receive a spinal fusion device, to be inserted in a disk space through the conduit.

91. The base of claim 90, wherein portions of the body contacts vertebral end caps during use.

92. The base of claim 90, wherein the body comprises a smooth outer surface.

93. The base of claim 90, wherein the at least one protrusion establishes a separation between adjacent vertebrae during use.

94. The base of claim 90, wherein the at least one protrusion is configured to maintain parallel orientation of a first vertebra and a second vertebra during use.

95. The base of claim 90, wherein the at least one protrusion is configured to inhibit rotation of the base when the at least one protrusion is positioned within the disk space during use.

96. The base of claim 90, wherein an end of the at least one protrusion has a wedge shape.

97. The base of claim 90, wherein a centerline of the conduit is parallel to a vertical axis of the body.

98. The base of claim 90, wherein a centerline of the conduit is angled oblique to a vertical axis of the body.

99. The base of claim 90, further comprising a flange removably coupled to the body, wherein the flange protects tissue and vessels adjacent to the base during use.

100. The base as defined in claim 99, wherein the flange is made of a semi-rigid material.

101. The base as defined in claim 99, wherein the flange comprises a collar configured to conform to the body to support the flange during use.

102. The base as defined in claim 99, wherein a lower surface of the flange curves to substantially match surface curvatures of vertebrae located adjacent to the base during use.

103. A base for use during a spinal fusion procedure, comprising:
   a body having a height of less than about 6 inches, said body comprising a conduit through the body;
   at least one protrusion extending from the body, the at least one protrusion positionable in a disk space between a first vertebra and a second vertebra;

a flange having a lower surface, wherein the flange is positionable around at least a portion of the body, wherein the flange is configured to protect tissue and vessels adjacent to the disk space during use; and wherein the lower surface of the flange curves during use to substantially match curvatures of surfaces of vertebrae adjacent to the holder; and wherein the conduit is configured to allow tools or devices for implanting a spinal fusion device, or for preparing a patient to receive a spinal fusion device, to be inserted in the disk space through the conduit.

104. The base as defined in claim 103, further comprising a sleeve, wherein an end of the sleeve is removably positionable in the conduit.

105. The base as defined in claim 104, further comprising a slot in a wall of the conduit, the slot configured to engage a distractor on an end of the sleeve during use.

106. The base as defined in claim 104, further comprising a shoulder in the conduit, the shoulder configured to limit insertion depth of the sleeve into the conduit.

107. The base as defined in claim 104, wherein the sleeve further comprises a view-port to provide increased visibility of a surgical site during use.

108. The base as defined in claim 103, wherein the at least one protrusion comprises serrations.

109. The base as defined in claim 103, wherein a height of the body is less than about four inches.

110. The base as defined in claim 103, wherein a height of the body is less than about two inches.

111. The base as defined in claim 103, further comprising a hole in the body, the hole configured to receive a fastener that couples the body to the first vertebra.

112. The base as defined in claim 111, wherein a centerline of the hole is angled oblique to a vertical axis of the body.

113. The base as defined in claim 111, wherein the hole comprises a shoulder configured to limit insertion depth of the fastener therein.

114. The base as defined in claim 103, wherein the bottom of the body is curved to substantially conform to curvatures of vertebrae adjacent to the holder during use.

115. The base as defined in claim 103, wherein at least a portion of the flange comprises a semi-rigid material.

116. The base as defined in claim 103, wherein the body comprises a smooth outer surface.

117. The base as defined in claim 103, wherein a portion of the body is configured to contact vertebral end caps during use.

118. The base as defined in claim 103, wherein the at least one protrusion is configured to inhibit rotation of the base when the at least one protrusion is positioned within the disk space during use.

119. The base as defined in claim 103, wherein an end of the at least one protrusion has a wedge shape.

120. The base as defined in claim 103, wherein the at least one protrusion comprises a surface configured to extend a portion of the conduit surface.

121. The base as defined in claim 103, wherein the at least one protrusion is configured to establish a substantially parallel spacing between a pair of adjacent vertebrae when positioned within the disk space during use.

122. The base as defined in claim 103, wherein a centerline of the conduit is angled oblique to a vertical axis of the body.

123. The base as defined in claim 103, wherein a centerline of the conduit is parallel to a vertical axis of the body.

124. The base as defined in claim 103, further comprising a rim on a portion of an outer surface of the body, wherein the rim is configured to engage the flange to support the flange during use.

125. The base as defined in claim 103, further comprising a groove on a portion of an outer surface of the body, wherein the flange is configured to engage the groove to support the flange on the body during use.

126. The base as defined in claim 103, wherein the flange further comprises a collar configured to conform to the body to support the flange during use.

127. A base for use during a spinal fusion procedure, comprising:

a body having a height of less than about six inches, said body comprising a conduit through the body;

at least one protrusion extending from the body, the at least one protrusion positionable in a disk space between a first vertebra and a second vertebra;

a flange positionable around the body, and wherein the flange is configured to protect tissue and vessels adjacent to the disk space during use;

a rim on a portion of an outer surface of the body, wherein the rim is configured to engage a portion of the flange to support the flange during use; and wherein the conduit is configured to allow tools or devices for implanting a spinal fusion device, or for preparing a patient to receive a spinal fusion device, to be inserted in the disk space through the conduit.

128. The base as defined in claim 127, further comprising a sleeve, and wherein an end of the sleeve is removably positionable in the conduit.

129. The base as defined in claim 128, further comprising a slot in a wall of the conduit, the slot configured to engage a distractor on an end of the sleeve during use.

130. The base as defined in claim 128, further comprising a shoulder in the conduit, the shoulder configured to limit insertion depth of the sleeve into the conduit.

131. The base as defined in claim 128, wherein the sleeve further comprises a view-port to provide increased visibility of a surgical site during use.

132. The base as defined in claim 127, wherein the at least one protrusion is inserted in the disk space between the first vertebra and the second vertebra to establish a separation distance between vertebrae during use.

133. The base as defined in claim 127, wherein the at least one protrusion comprises sides and further comprises serrations on at least one side of the at least one protrusion.

134. The base as defined in claim 127, wherein a height of the body is less than about four inches.

135. The base as defined in claim 127, wherein a height of the body is less than about two inches.

136. The base as defined in claim 127, further comprising a hole in the body, the hole configured to receive a fastener that couples the body to the first vertebra.

137. The base as defined in claim 136, wherein a centerline of the hole is angled oblique to a vertical axis of the body.

138. The base as defined in claim 127, wherein a bottom of the body is curved to substantially conform to curvatures of vertebrae adjacent to the holder during use.

139. The base as defined in claim 127, wherein at least a portion of the flange comprises a semi-rigid material.

140. The base as defined in claim 127, wherein the body comprises a smooth outer surface.

141. The base as defined in claim 127, wherein a portion of the body is configured to contact vertebral end caps during use.

142. The base as defined in claim 136, wherein the hole comprises a shoulder configured to limit insertion depth of the fastener therein.

143. The base as defined in claim 127, wherein the at least one protrusion extends from the body on the same surface as the body contacts vertebrae.

144. The base as defined in claim 127, wherein the at least one protrusion is positioned on the body to inhibit rotation of the base when the at least one protrusion is positioned within the disk space during use.

145. The base as defined in claim 132, wherein an end of the at least one protrusion has a wedge shape.

146. The base as defined in claim 132, wherein the at least one protrusion comprises a surface configured to extend a portion of the conduit surface between the vertebrae.

147. The base as defined in claim 132, wherein the at least one protrusion comprises a surface for contacting vertebral end caps during use.

148. The base as defined in claim 147, wherein the at least one protrusion is shaped to maintain a parallel orientation of the first vertebra and the second vertebra after insertion of the at least one protrusion in the disk space.

149. The base as defined in claim 127, wherein a centerline of the conduit is angled oblique to the vertical axis of the body.

150. The base as defined in claim 127, wherein a centerline of the conduit is parallel to the vertical axis of the body.

151. The base as defined in claim 120, wherein the conduit abuts and aligns with the disk space between the first vertebra and the second vertebra.

152. The base as defined in claim 127, further comprising a groove on a portion of an outer surface of the body, wherein the groove is configured to engage the inner edge of the flange to support the flange during use.

153. The base as defined in claim 127, wherein the flange further comprises a collar configured to conform to the body to support the flange during use.

154. A base for use during a spinal fusion procedure, comprising:
   a body having a height of less than about six inches, said body comprising a conduit through the body;
   at least one protrusion extending from the body, the at least one protrusion positionable in a disk space between a first vertebra and a second vertebra;
   a flange positionable around the body, wherein the flange is configured to protect tissue and vessels adjacent to the disk space during use;
   a groove on a portion of an outer surface of the body, wherein the groove is configured to engage a portion of the flange to support the flange during use; and
   wherein the conduit is configured to allow tools or devices for implanting a spinal fusion device, or for preparing a patient to receive a spinal fusion device, to be inserted in the disk space through the conduit.

155. The base as defined in claim 154, further comprising a sleeve, and wherein an end of the sleeve is removably positionable in the conduit.

156. The base as defined in claim 155, further comprising a slot in a wall of the conduit, the slot configured to engage a distractor on an end of the sleeve during use.

157. The base as defined in claim 155, further comprising a shoulder in the conduit, the shoulders configured to limit insertion depth of the sleeve into the conduit.

158. The base as defined in claim 155, wherein the sleeve further comprises a view-port to provide increased visibility of a surgical site during use.

159. The base as defined in claim 154, wherein the at least one protrusion comprises serrations.

160. The base as defined in claim 154, wherein a height of the body is less than about four inches.

161. The base as defined in claim 154, wherein a height of the body is less than about two inches.

162. The base as defined in claim 154, further comprising a hole in the body, the hole configured to receive a fastener that couples the body to the first vertebra.

163. The base as defined in claim 162, wherein the hole comprises a shoulder configured to limit insertion depth of the fastener therein.

164. The base as defined in claim 154, wherein a bottom of the body is curved to substantially conform to curvatures of vertebrae adjacent to the holder during use.

165. The base as defined in claim 154, wherein at least a portion of the flange comprises a semi-rigid material.

166. The base as defined in claim 154, wherein the body comprises a smooth outer surface.

167. The base as defined in claim 154, wherein a portion of the body is configured to contact vertebral end caps during use.

168. The base as defined in claim 154, wherein the at least one protrusion is configured to inhibit rotation of the base when the at least one protrusion is positioned within the disk space during use.

169. The base as defined in claim 154, wherein an end of the at least one protrusion has a wedge shaped.

170. The base as defined in claim 154, wherein a surface of the at least one protrusion is an extension of a surface of the conduit.

171. The base as defined in claim 154, wherein the at least one protrusion is configured to establish a substantially parallel spacing between adjacent vertebrae during use.

172. The base as defined in claim 154, wherein a centerline of the conduit is angled oblique to a vertical axis of the body.

173. The base as defined in claim 154, wherein a centerline of the conduit is parallel to the vertical axis of the body.

174. The base as defined in claim 154, wherein the conduit abuts and aligns with the disk space between the first vertebra and the second vertebra.

175. The base as defined in claim 154, wherein the flange further comprises a collar configured to conform to the body to support the flange during use.

176. A base for use during a spinal fusion procedure, comprising:
   a body having a height of less than about 6 inches, said body comprising a conduit through the body;
   at least one protrusion extending from the body, the at least one protrusion positionable in a disk space between a first vertebra and a second vertebra;
   a flange comprising a collar, wherein the collar is configured to conform to the body to support the flange during use, wherein the flange is positionable around the body, and wherein the flange is configured to protect tissue and vessels adjacent to the disc space during use; and
   wherein the conduit is configured to allow tools or devices for implanting a spinal fusion device, or for preparing a patient to receive a spinal fusion device, to be inserted in the disk space through the conduit.

177. The base as defined in claim 176, further comprising a sleeve, and wherein an end of the sleeve is removably positionable in the conduit.

178. The base as defined in claim 177, further comprising a slot in a wall of the conduit, the slot configured to engage a distractor on an end of the sleeve during use.

179. The base as defined in claim 177, further comprising a shoulder in the conduit, the shoulder configured to limit insertion depth of the sleeve into the conduit.

180. The base as defined in claim 177, wherein the sleeve further comprises a view-port to provide increased visibility of a surgical site during use.

181. The base as defined in claim 176, wherein the at least one protrusion is inserted in the disk space between the first vertebra and the second vertebra to establish a separation distance between the vertebrae during use.

182. The base as defined in claim 176, wherein the at least one protrusion comprises sides and further comprises serrations on at least one side of the at least one protrusion.

183. The base as defined in claim 176, wherein a height of the body is less than about four inches.

184. The base as defined in claim 176, wherein a height of the body is less than about two inches.

185. The base as defined in claim 176, further comprising a hole in the body, the hole configured to receive a fastener that couples the body to the first vertebra.

186. The base as defined in claim 185, wherein a centerline of the hole is angled oblique to a vertical axis of the body.

187. The base as defined in claim 176, wherein the bottom of the body is curved to substantially conform to curvatures of vertebrae adjacent to the holder during use.

188. The base as defined in claim 176, wherein at least a portion of the flange comprises a semi-rigid material.

189. The base as defined in claim 176, wherein the body comprises a smooth outer surface.

190. The base as defined in claim 176, wherein a portion of the body is configured to contact vertebral end caps during use.

191. The base as defined in claim 185, wherein the hole comprises a shoulder configured to limit insertion depth of the fastener therein.

192. The base as defined in claim 176, wherein the at least one protrusion extends from the body on the same surface as the body contacts the first vertebra and the second vertebra.

193. The base as defined in claim 176, wherein the at least one protrusion is positioned on the body to inhibit rotation of the base when the at least one protrusion is positioned within the disk space during use.

194. The base as defined in claim 181, wherein an end of the at least one protrusion has a wedge shape.

195. The base as defined in claim 181, wherein the at least one protrusion comprises a surface configured to extend a portion of the conduit surface between the vertebrae.

196. The base as defined in claim 181, wherein the at least one protrusion comprises a surface for contacting vertebral end caps during use.

197. The base as defined in claim 196, wherein the at least one protrusion is shaped to maintain a parallel orientation of the first vertebra and the second vertebra after insertion of the at least one protrusion in the disk space.

198. The base as defined in claim 176, wherein a centerline of the conduit is angled oblique to the vertical axis of the body.

199. The base as defined in claim 176, wherein a centerline of the conduit is parallel to the vertical axis of the body.

200. The base as defined in claim 176, wherein the conduit abuts and aligns with the disk space between the first vertebra and the second vertebra.

201. A holder for use with a sleeve during a spinal fusion procedure comprising:
- a body;
- a first conduit through the body;
- a second conduit through the body;
- a protrusion from a bottom of the body, the protrusion configured to couple the body within a disk space between a first vertebra and a second vertebra; and wherein the sleeve is removably positionable within the first conduit or the second conduit, and wherein the conduit and the sleeve are configured to allow for insertion of tools or devices for implanting a spinal fusion device, or for preparing a patient to receive a spinal fusion device, in the disk space.

202. The holder as defined in claim 201, further comprising a shoulder in the first conduit, wherein the shoulder limits insertion depth of the sleeve into the first conduit.

203. The holder as defined in claim 201, wherein the protrusion establishes a separation distance between the vertebrae during use.

204. The holder as defined in claim 201, wherein the protrusion has sides and further comprising serrations on at least one side of the protrusion.

205. The holder as defined in claim 201, wherein the protrusion is located between exit holes of the first and second conduits in the bottom of the body.

206. The holder as defined in claim 205, further comprising a second protrusion extending from the bottom of the body adjacent to a side of the exit hole of the first conduit opposite the first protrusion, the second protrusion positionable between adjacent vertebrae during use.

207. The holder as defined in claim 206, wherein the second protrusion further comprises serrations on a side of the second protrusion.

208. The holder as defined in claim 201 further comprising a second protrusion extending from the bottom of the body adjacent to a side of the first conduit, and a third protrusion extending from the bottom of the body adjacent to a side of the exit hole of the second conduit, wherein the first protrusion is positioned between the second protrusion and the third protrusion.

209. The holder as defined in claim 208, wherein the second protrusion further comprises serrations on a side of the second protrusion.

210. The holder as defined in claim 201, further comprising a hole passing through the body, the hole configured to receive a fastener that couples the holder to a vertebra during use.

211. The holder as defined in claim 210, wherein the hole passes through the body at an oblique angle relative to a vertical axis of the body.

212. The holder as defined in claim 201, wherein the bottom of the body is curved to substantially conform to curvatures of vertebrae adjacent to the holder during use.

213. The holder as defined in claim 201, further comprising a flange, the flange having an inner edge, an outer edge, a lower surface, and an upper surface, wherein the flange is positionable around the body, and wherein the flange is configured to protect tissue and vessels adjacent to the first vertebra and second vertebra during use.

214. The holder as defined in claim 213, wherein the flange is made of a semi-rigid material.

215. The holder as defined in claim 213, wherein a lower surface of the flange curves during use to substantially match curvatures of surfaces of vertebrae adjacent to the holder.

216. The holder as defined in claim 213, wherein the flange further comprises an elastic collar configured to conform to the shape of the body during use to support the flange.

217. The holder as defined in claim 213, further comprising a rim on a portion of an outer surface of the body, wherein the rim is configured to engage the lower surface the flange during use.

218. The holder as defined in claim 213, further comprising a groove on a portion of an outer surface of the body, wherein the groove is configured to engage the inner edge of the flange during use.

219. The holder as defined in claim 201, wherein the first conduit further comprises a slot on an inner surface, the slot configured to engage a distractor on an end of the sleeve during use.

220. The holder as defined in claim 201 wherein the first and second conduits are substantially parallel.

221. The holder as defined in claim 201, wherein the conduits are angled relative to each other.

222. The holder as defined in claim 221, wherein a distance between a centerline of the first conduit and a centerline of the second conduit at a top of the body is greater than a distance between centerlines of the conduits at the bottom of the body.

223. The holder as defined in claim 222, wherein an angle between the centerlines of the conduits is less than about 30 degrees.

224. The holder as defined in claim 222, wherein an angle between the centerlines of the conduits is less than about 20 degrees.

225. The holder as defined in claim 222, wherein an angle between the centerlines of the conduits is between about 2 degrees and about 10 degrees.

226. The holder as defined in claim 201, wherein the body further comprises two sides, and wherein the sides flare such that a largest width of the body measured from side to side is proximate the bottom of the body.

227. The holder as defined in claim 201, further comprising a first hole and a second hole passing through the body and wherein the first hole and the second hole are configured to receive fasteners for coupling the holder to vertebrae during use.

228. The holder as defined in claim 227, wherein the first hole and the second hole are obliquely angled through the body relative to a vertical axis of the body.

229. The holder as defined in claim 227, wherein the body further comprises:
a first side and a second side; and
wherein the holes are located between the first and second conduits;
wherein an entry of the first hole is located on a top of the body proximate the first side, and an exit of the first hole is located on the bottom of the body proximate the second side; and
wherein an entry of the second hole is located on the top of the body proximate the second side, and an exit for the second hole is located on the bottom of the body proximate the first side.

230. The holder as defined in claim 227, wherein the body further comprises:
a first side and a second side; and
an opening in a top of the body, the opening having a bottom;
wherein an entry of the first hole is located substantially at the bottom of the opening near the first side, and an exit of the first hole is located on the bottom of the body proximate the first side; and
wherein an entry for the second hole is located substantially at the bottom of the opening near the second side, and an exit for the second hole is located on the bottom of the body proximate the second side.

231. The holder as defined in claim 230, the opening is located between the first conduit and the second conduit.

232. The holder as defined in claim 201, wherein a height of the body is less than about six inches.

233. The holder as defined in claim 201, wherein a height of the body is less than about four inches.

234. The holder as defined in claim 201, wherein a height of the body is less than about two inches.

235. The holder as defined in claim 201, wherein a portion of the first conduit overlaps a portion of the second conduit.

236. The holder as defined in claim 201, wherein the sleeve further comprises a view-port to provide increased visibility of a surgical site during use.

237. The holder as defined in claim 201, wherein the body comprises a smooth outer surface.

238. The holder as defined in claim 201, wherein a portion of the body contacts vertebral end caps during use.

239. The holder as defined in claim 210, wherein the hole comprises a shoulder configured to limit an insertion depth of the fastener therein.

240. The holder as defined in claim 201, wherein the first conduit and the second conduit comprise shoulders configured to limit an insertion depth of a sleeve into the conduits.

241. The holder as defined in claim 201, wherein the first conduit and the second conduit are angled oblique to a vertical axis of the body.

242. The holder as defined in claim 220, wherein the first and second conduits are substantially parallel to a vertical axis of the body.

243. The holder as defined in claim 221, wherein a distance between a centerline of the first conduit and a centerline of the second conduit at a top of the body is less than a distance between centerlines of the conduits at a bottom of the body.

244. The holder as defined in claim 227, wherein the first hole and the second hole comprise, shoulders configured to engage heads of the fasteners.

245. The holder as defined in claim 205, wherein the protrusion comprises a surface configured to extend a portion of the first conduit opening surface between the first vertebra and the second vertebra.

246. The holder as defined in claim 245, wherein the protrusion comprises a second surface configured to extend a portion of the second conduit opening surface between the first vertebra and the second vertebra.

247. The holder as defined in claim 205, wherein the protrusion is configured to inhibit rotation of the body within the disk space during use.

248. The holder as defined in claim 205, wherein an end of the protrusion has a wedge shape.

249. The holder as defined in claim 248, wherein the protrusion is configured to establish a substantially parallel spacing between the first vertebra and the second vertebrae.

250. The holder as defined in claim 206, wherein the second protrusion comprises a surface configured to extend a surface of the first conduit opening surface into the disk space.

251. The holder as defined in claim 206, wherein the second protrusion is configured to inhibit rotation of the body within the disk space during use.

252. The holder as defined in claim 206, wherein an end of the second protrusion has a wedge shape.

253. The holder as defined in claim 208, wherein the first protrusion comprises a surface configured to extend an inner surface of the first conduit into the disk space during use.

254. The holder as defined in claim 253, wherein the first protrusion comprises a second surface configured to extend an inner surface of the second conduit into the disk space.

255. The holder as defined in claim 253, wherein the second protrusion comprises a surface configured to extend an inner surface of the first conduit into the disk space.

256. The holder as defined in claim 253, wherein the third protrusion comprises a surface configured to extend an inner surface of the second conduit into the disk space.

257. The holder as defined in claim 208, wherein the first protrusion, the second protrusion and the third protrusion are configured to inhibit rotation of the body within the disk space during use.

258. The holder as defined in claim 208, wherein an end of the first protrusion has a wedge shape.

259. The holder as defined in claim 208, wherein an end of the second protrusion has a wedge shape.

260. The holder as defined in claim 208, wherein an end of the third protrusion has a wedge shape.

261. A holder for use with a removable sleeve during a spinal fusion procedure, comprising:
 a body;
 at least one protrusion extending from the body;
 a conduit through the body;
 a shoulder in the conduit, the shoulder configured to limit insertion depth of the sleeve into the conduit; and
 wherein an end of the sleeve is removably positionable in the conduit during use, and wherein the sleeve is configured to allow tools or devices for implanting a spinal fusion device, or for preparing a patient to receive a spinal fusion device, to be inserted in a disk space through the sleeve and through the conduit.

262. The holder of claim 261, wherein a height of the body is less than about six inches.

263. The holder of claim 261, wherein a height of the body is less than about three inches.

264. The holder of claim 261, wherein a height of the body is less than about two inches.

265. The holder of claim 261, wherein a bottom of the body is shaped to substantially conform to surfaces of vertebrae adjacent to the holder during use.

266. The holder of claim 261, wherein portions of the body contact end caps of adjacent vertebrae during use.

267. The holder of claim 261, wherein the body comprises a smooth outer surface.

268. The holder of claim 261, further comprising a slot in a wall of the conduit, the slot configured to engage a distractor on an end of the sleeve during use.

269. The holder of claim 261, further comprising a flange removably coupled to the body, wherein the flange protects tissue and vessels adjacent to the holder during use.

270. The holder of claim 269, wherein the flange is made of a semi-rigid material.

271. The holder of claim 269, wherein the flange comprises an inner edge, an outer edge, a lower surface, and an upper surface, and wherein the flange is positionable substantially around the body during use.

272. The holder of claim 271, wherein the flange comprises a collar configured to conform to the shape of the body to support the flange during use.

273. The holder of claim 271, wherein a lower surface of the flange curves during use to substantially match surface curvatures of vertebrae adjacent to the holder.

274. The holder of claim 271, wherein the body comprises a rim to engage and support the inner surface of the flange during use.

275. The holder of claim 261, wherein the at least one protrusion is inserted in the disk space between a first vertebra and a second vertebra to establish a separation between the vertebrae during use.

276. The holder of claim 273, wherein the at least one protrusion is configured to provide a substantially parallel orientation between the first vertebra and the second vertebra.

277. The holder of claim 275, wherein the at least one protrusion is configured to inhibit rotation of the holder when the at least one protrusion is positioned in the disk space during use.

278. The holder of claim 273, wherein the at least one protrusion is configured to couple the body to the first vertebra and the second vertebra.

279. The holder of claim 278, wherein the at least one protrusion comprises serrations.

280. The holder of claim 278, wherein an end of the at least one protrusion has a wedge shape.

281. A holder for use with a removable sleeve during a spinal fusion procedure, comprising:
 a body;
 at least one protrusion extending from the body, wherein the at least one protrusion comprises serrations on at least one side of the at least one protrusion;
 a conduit through the body; and
 wherein an end of the sleeve is removably positionable in the conduit during use, and wherein the sleeve is configured to allow tools or devices for implanting a spinal fusion device, or for preparing a patient to receive a spinal fusion device, to be inserted in a disk space through the sleeve and through the conduit.

282. The holder of claim 281, wherein a height of the body is less than about six inches.

283. The holder of claim 281, wherein a height of the body is less than about three inches.

284. The holder of claim 281, wherein a height of the body is less than about two inches.

285. The holder of claim 281, wherein a bottom of the body is shaped to substantially conform to surfaces of vertebrae adjacent to the holder during use.

286. The holder of claim 281, wherein portions of the body contact end caps of adjacent vertebrae during use.

287. The holder of claim 281, wherein the body comprises a smooth outer surface.

288. The holder of claim 281, further comprising a slot in a wall of the conduit, the slot configured to engage a distractor on an end of the sleeve during use.

289. The holder of claim 281, further comprising a flange removably coupled to the body, wherein the flange protects tissue and vessels adjacent to the holder during use.

290. The holder of claim 289, wherein the flange is made of a semi-rigid material.

291. The holder of claim 289, wherein the flange comprises a collar configured to conform to the body to support the flange during use.

292. The holder of claim 289, wherein a lower surface of the flange curves to substantially match surface curvatures of vertebrae located adjacent to the holder during use.

293. The holder of claim 281, wherein the at least one protrusion establishes a separation between adjacent vertebrae during use.

294. The holder of claim 281, wherein the at least one protrusion is configured to provide a substantially parallel orientation between a first vertebra and a second vertebra during use.

295. The holder of claim 281, wherein the at least one protrusion is configured to inhibit rotation of the holder when the at least one protrusion is positioned within the disk space during use.

296. The holder of claim 281, wherein an end of the at least one protrusion has a wedge shape.

297. A holder for use with a sleeve during a spinal fusion procedure, comprising:
 a body;

at least one protrusion extending from the body;
a flange, the flange having an inner edge, an outer edge, a lower surface and an upper surface, wherein the flange is positionable substantially around the body, and wherein the flange is configured to protect tissue and vessels adjacent to a disk space during use;
a conduit through the body; and
wherein an end of the sleeve is removably positionable in the conduit during use, and wherein the sleeve is configured to allow tools or devices for implanting a spinal fusion device, or for preparing a patient to receive a spinal fusion device, to be inserted in the disk space through the sleeve and through the conduit.

298. The holder of claim 297, wherein a height of the body is less than about six inches.

299. The holder of claim 297, wherein a height of the body is less than about three inches.

300. The holder of claim 297, wherein a height of the body is less than about two inches.

301. The holder of claim 297, wherein a bottom of the body is shaped to substantially conform to surfaces of vertebrae adjacent to the holder during use.

302. The holder of claim 297, wherein portions of the body contact end caps of adjacent vertebrae during use.

303. The holder of claim 281, wherein the body comprises a smooth outer surface.

304. The holder of claim 281, further comprising a slot in a wall of the conduit, the slot configured to engage a distractor on an end of the sleeve during use.

305. The holder of claim 281, wherein the at least one protrusion establishes a separation between adjacent vertebrae during use.

306. The holder of claim 305, wherein the at least one protrusion is configured to maintain parallel orientation of a first vertebra and a second vertebra.

307. The holder of claim 305, wherein the at least one protrusion is configured to inhibit rotation of the holder when the at least one protrusion is positioned within the disk space during use.

308. The holder of claim 305, wherein an end of the at least one protrusion has a wedge shape.

309. The holder of claim 281, wherein the flange is made of a semi-rigid material.

310. The holder of claim 281, wherein the lower surface of the flange curves to substantially match surface curvatures of vertebrae located adjacent to the holder during use.

311. The holder of claim 281, further comprising a rim on a portion of an outer surface of the body, wherein the rim is configured to engage the lower surface of the flange to support the flange during use.

312. The holder of claim 281, further comprising a groove on a portion of an outer surface of the body, wherein the groove is configured to engage the inner edge of the flange to support the flange during use.

313. The holder of claim 281, wherein the flange further comprises a collar configured to conform to the body to support the flange during use.

314. A holder for use with a sleeve during a spinal fusion procedure, comprising:
a body;
at least one protrusion extending from the body;
a conduit through the body; and
a slot in a wall of the conduit, the slot configured to engage a distractor on an end of the sleeve during use;
wherein an end of the sleeve is removably positionable in the conduit during use, and wherein the sleeve is configured to allow tools or devices for implanting a spinal fusion device, or for preparing a patient to receive a spinal fusion device, to be inserted in a disk space through the sleeve and through the conduit.

315. The holder of claim 314, wherein a height of the body is less than about six inches.

316. The holder of claim 314, wherein a height of the body is less than about three inches.

317. The holder of claim 314, wherein a height of the body is less than about two inches.

318. The holder of claim 314, wherein a bottom of the body is shaped to substantially conform to surfaces of vertebrae adjacent to the holder during use.

319. The holder of claim 314, wherein portions of the body contact end caps of adjacent vertebrae during use.

320. The holder of claim 314, wherein the body comprises a smooth outer surface.

321. The holder of claim 314, further comprising a flange removably coupled to the body, wherein the flange protects tissue and vessels adjacent to the holder during use.

322. The holder of claim 321, wherein the flange is made of a semi-rigid material.

323. The holder of claim 321, wherein the flange comprises a collar configured to conform to the body to support the flange during use.

324. The holder of claim 321, wherein a lower surface of the flange curves during use to substantially match curvatures of surfaces of vertebrae adjacent to the holder.

325. The holder of claim 321, wherein the body comprises a rim to engage and support the flange during use.

326. The holder of claim 314, wherein the at least one protrusion establishes a separation between adjacent vertebrae during use.

327. The holder of claim 326, wherein the at least one protrusion is configured to maintain parallel orientation of a first vertebra and a second vertebra.

328. The holder of claim 326, wherein the at least one protrusion is configured to inhibit rotation of the holder when the at least one protrusion is positioned within the disk space during use.

329. The holder of claim 326, wherein an end of the at least one protrusion has a wedge shape.

330. A holder for use with a sleeve during a spinal fusion procedure, comprising:
a body, wherein a bottom of the body comprises a surface configured to substantially conform to surfaces of vertebrae adjacent to the holder during use;
at least one protrusion extending from the body;
a conduit through the body; and
wherein an end of the sleeve is removably positionable in the conduit during use, and wherein the sleeve is configured to allow tools or devices for implanting a spinal fusion device, or for preparing a patient to receive a spinal fusion device, to be inserted in a disk space through the sleeve and through the conduit.

331. The holder of claim 330, wherein a height of the body is less than about six inches.

332. The holder of claim 330, wherein a height of the body is less than about three inches.

333. The holder of claim 330, wherein a height of the body is less than about two inches.

334. The holder of claim 330, wherein portions of the body contact end caps of adjacent vertebrae during use.

335. The holder of claim 330, wherein the body comprises a smooth outer surface.

336. The holder of claim 330 further comprising a flange removably coupled to the body, wherein the flange protects tissue and vessels adjacent to the holder during use.

337. The holder of claim 336, wherein the flange is made of a semi-rigid material.

338. The holder of claim 336, wherein the flange comprises a collar configured to conform to the body to support the flange during use.

339. The holder of claim 336, wherein a lower surface of the flange curves to substantially match surface curvatures of vertebrae located adjacent to the holder during use.

340. The holder of claim 336, wherein the body comprises a rim to engage and support the flange during use.

341. The holder of claim 330, wherein the at least one protrusion is configured to establish a parallel spacing between adjacent vertebrae during use.

342. The holder of claim 330, therein the at least one protrusion is configured to inhibit rotation of the holder when the at least one protrusion is positioned within the disk space during use.

343. The holder of claim 330, wherein an end of the at least one protrusion has a wedge shape.

344. A holder for use with a sleeve during a spinal fusion procedure, comprising:
    a body;
    at least one protrusion extending from the body, the at least one protrusion positionable in a disk space between a first vertebra and a second vertebra;
    a conduit through the body;
    a flange positionable around the body, wherein the flange is configured to protect tissue and vessels adjacent to the disk space during use;
    wherein a lower surface of the flange curves during use to substantially match surface curvatures of vertebrae adjacent to the holder; and
    wherein an end of the sleeve is removably positionable in the conduit during use, and wherein the sleeve is configured to allow tools or devices for implanting a spinal fusion device, or for preparing a patient to receive a spinal fusion device, to be inserted in the disk space through the sleeve and through the conduit.

345. The holder as defined in claim 344, further comprising a shoulder in the conduit, the shoulder configured to limit insertion depth of the sleeve into the conduit.

346. The holder as defined in claim 344, further comprising a slot in a wall of the conduit, the slot configured to engage a distractor on an end of the sleeve during use.

347. The holder as defined in claim 344, wherein a centerline of the conduit is angled oblique to a vertical axis of the body.

348. The holder as defined in claim 344, wherein a centerline of the conduit is parallel to a vertical axis of the body.

349. The holder as defined in claim 344, wherein the conduit abuts and aligns with the disk space between the first vertebra and the second vertebra during use.

350. The holder as defined in claim 344, wherein the body comprises a smooth outer surface.

351. The holder as defined in claim 334, wherein portions of the body reside on vertebral end caps during use.

352. The holder as defined in claim 344, wherein a height of the body is less than about six inches.

353. The holder as defined in claim 344, wherein a height of the body is less than about four inches.

354. The holder as defined in claim 344, wherein a height of the body is less than about two inches.

355. The holder as defined in claim 344, further comprising a hole in the body, the hole configured to receive a fastener that couples the body to the first vertebra.

356. The holder as defined in claim 355, wherein a centerline of the hole is angled oblique to a vertical axis of the body.

357. The holder as defined in claim 355, wherein the hole comprises a shoulder configured to limit the insertion of the fastener through the body.

358. The holder as defined in claim 344, wherein the sleeve further comprises a view-port to provide increased visibility of a surgical site during use.

359. The holder as defined in claim 344, wherein the at least one protrusion is inserted between the first vertebra and the second vertebra to establish a separation distance between the vertebrae during use.

360. The holder as defined in claim 344, wherein the at least one protrusion comprises sides and further comprising serrations on at least one side of the at least one protrusion.

361. The holder as defined in claim 359, wherein an end of the at least one protrusion has a wedge shape.

362. The holder as defined in claim 359, wherein the at least one protrusion extends from a surface of the body adjacent to vertebrae.

363. The holder as defined in claim 359, wherein the at least one protrusion comprises a surface configured to extend a portion of the conduit opening surface between the first vertebra and the second vertebra.

364. The holder as defined in claim 359, wherein the at least one protrusion is configured to inhibit rotation of the body wherein the at least one protrusion is positioned within the disk space during use.

365. The holder as defined in claim 359, wherein the at least one protrusion comprises a surface to maintain parallel orientation of the adjacent vertebrae during use.

366. The holder as defined in claim 344, wherein the flange is made of a semi-rigid materials.

367. The holder as defined in claim 344, further comprising a rim on a portion of an outer surface of the body, wherein the rim is configured to engage the lower surface of the flange to support the flange during use.

368. The holder as defined in claim 344, further comprising a groove on a portion of an outer surface of the body, wherein the groove is configured to engage the inner edge of the flange to support the flange during use.

369. The holder as defined in claim 344, wherein the flange further comprises a collar configured to conform to the body to support the flange during use.

370. A holder for use with a sleeve during a spinal fusion procedure, comprising:
    a body;
    at least one protrusion extending from the body, the at least one protrusion positionable in a disk space between a first vertebra and a second vertebra;
    a conduit through the body;
    a flange positionable around the body, wherein the flange is configured to protect tissue and vessels adjacent to the disk space during use;
    a groove on a portion of an outer surface of the body, wherein the flange is configured to engage the groove to support the flange during use; and
    wherein an end of the sleeve is removably positionable in the conduit during use, and wherein the sleeve is configured to allow tools or devices for implanting a spinal fusion device, or for preparing a patient to receive a spinal fusion device, to be inserted in the disk space through the sleeve and through the conduit.

371. The holder as defined in claim 370, further comprising a shoulder in the conduit, the shoulder configured to limit insertion depth of the sleeve into the conduit.

372. The holder as defined in claim 370, further comprising a slot in a wall of the conduit the slot configured to engage a distractor on an end of the sleeve during use.

373. The holder as defined in claim 370, wherein a centerline of the conduit is angled oblique to a vertical axis of the body.

374. The holder as defined in claim 370, wherein a centerline of the conduit is parallel.

375. The holder as defined in claim 370, wherein the conduit abuts and aligns with the disk space between the first vertebra and the second vertebra.

376. The holder as defined in claim 371, wherein the conduit is configured to allow tools and devices for implanting to pass therein.

377. The holder as defined in claim 370, wherein the body comprises a smooth outer surface.

378. The holder as defined in claim 370, wherein portions of the body reside on vertebral end caps during use.

379. The holder as defined in claim 370, wherein a height of the body is less than about six inches.

380. The holder as defined in claim 370, wherein a height of the body is less than about four inches.

381. The holder as defined in claim 370, wherein a height of the body is less than about two inches.

382. The holder as defined in claim 370, further comprising a hole in the body, the hole configured to receive a fastener that couples the body to the first vertebra.

383. The holder as defined in claim 382, wherein a centerline of the hole is angled oblique to a vertical axis of the body.

384. The holder as defined in claim 382, wherein the hole comprises a shoulder configured to limit insertion depth of the fastener through the body.

385. The holder as defined in claim 370, wherein the sleeve further comprises a view-port to provide increased visibility of a surgical site during use.

386. The holder as defined in claim 370, wherein the at least one protrusion is inserted between the first vertebra and the second vertebra to establish a separation distance between the vertebrae during use.

387. The holder as defined in claim 370, wherein the at least one protrusion comprises sides and further comprising serrations on at least one side of the at least one protrusion.

388. The holder as defined in claim 386, wherein an end of the at least one protrusion has a wedge shape.

389. The holder as defined in claim 386, wherein the at least one protrusion is configured to inhibit rotation of the body when the at least one protrusion is positioned in the disk space during use.

390. The holder as defined in claim 386, wherein the at least one protrusion comprises a surface to maintain parallel orientation of the adjacent vertebrae.

391. The holder as defined in claim 370, wherein the flange is made of a semi-rigid material.

392. The holder as defined in claim 370, wherein the flange further comprises a collar configured to conform to the body to support the flange during use.

393. A holder for use with a sleeve during a spinal fusion procedure, comprising:
  a body;
  at least one protrusion extending from the body, the at least one protrusion positionable in a disk space between a first vertebra and a second vertebra;
  a conduit through the body;
  a flange positionable around at least a portion of the body, wherein the flange is configured to protect tissue and vessels adjacent to the disk space during use, and
  wherein the lower surface of the flange curves during use to substantially match surface curvatures of vertebrae adjacent to the holder;
  a rim on a portion of an outer surface of the body, wherein the rim is configured to engage the flange to support the flange during us; and
  wherein an end of the sleeve is removably positionable in the conduit during use, and wherein the sleeve is configured to allow tools or devices for implanting a spinal fusion device, or for preparing a patient to receive a spinal fusion device, to be inserted in the disk space through the sleeve and through the conduit.

394. The holder as defined in claim 393, further comprising a shoulder in the conduit, the shoulder configured to limit insertion depth of the sleeve into the conduit.

395. The holder as defined in claim 393, further comprising a slot in a wall of the conduit, the slot configured to engage a distractor on an end of the sleeve during use.

396. The holder as defined in claim 393, wherein a centerline of the conduit is angled oblique to a vertical axis of the body.

397. The holder as defined in claim 393, wherein a centerline of the conduit is parallel to a vertical axis of the body.

398. The holder as defined in claim 393, wherein the conduit abuts and aligns with the disk space between the first vertebra and the second vertebra.

399. The holder as defined in claim 394, wherein the conduit is configured to allow tools and devices for implanting to pass therein.

400. The holder as defined in claim 393, wherein the body comprises a smooth outer surface.

401. The holder as defined in claim 393, wherein portions of the body reside on vertebral end caps during use.

402. The holder as defined in claim 393, wherein a height of the body is less than about six inches.

403. The holder as defined in claim 393, wherein a height of the body is less than about four inches.

404. The holder as defined in claim 393, wherein a height of the body is less than about two inches.

405. The holder as defined in claim 393, further comprising a hole in the body, the hole configured to receive a fastener that couples the body to the first vertebra.

406. The holder as defined in claim 405, wherein a centerline of the hole is angled oblique to a vertical axis of the body.

407. The holder as defined in claim 405, wherein the hole comprises a shoulder configured to limit insertion depth of the fastener through the body.

408. The holder as defined in claim 393, wherein the sleeve further comprises a view-port to provide increased visibility of a surgical site during use.

409. The holder as defined in claim 393, wherein the at least one protrusion is inserted between adjacent vertebrae to establish a separation distance between the vertebrae during use.

410. The holder as defined in claim 409, wherein an end of the at least one protrusion has a wedge shape.

411. The holder as defined in claim 409, wherein the at least one protrusion is configured to inhibit rotation of the body when the at least one protrusion is positioned within the disk space during use.

412. The holder as defined in claim 409, wherein the at least one protrusion is configured to establish a substantially parallel orientation between the vertebrae during use.

413. The holder as defined in claim 393, wherein the at least one protrusion comprises serrations configured to couple the holder to at least one of the vertebrae.

414. The holder as defined in claim 393, wherein the flange is made of a semi-rigid material.

415. The holder as defined in claim 393 wherein the flange further comprises a collar configured to conform to the body during use.

416. A holder for use with a sleeve during a spinal fusion procedure, comprising:
  a body;
  at least one protrusion extending from the body, the at least one protrusion positionable in a disk space between a first vertebra and a second vertebra;
  a conduit through the body;
  a flange comprising a collar including elastic material configured to attach the flange to the body during use, wherein the flange is positionable around the body, and wherein the flange is configured to protect tissue and vessels adjacent to the first vertebra and second vertebra during use; and
  wherein an end of the sleeve is removably positionable in the conduit during use, and wherein the sleeve is configured to allow tools or devices for implanting a spinal fusion device, or for preparing a patient to receive a spinal fusion device, to be inserted in the disk space through the sleeve and through the conduit.

417. The holder as defined in claim 416, further comprising a shoulder in the conduit, the shoulder configured to limit insertion depth of the sleeve into the conduit.

418. The holder as defined in claim 416, further comprising a slot in a wall of the conduit, the slot configured to engage a distractor on an end of the sleeve during use.

419. The holder as defined in claim 416, wherein a centerline of the conduit is angled oblique to the vertical axis of the body.

420. The holder as defined in claim 416, wherein a centerline of the conduit is parallel to the vertical axis of the body.

421. The holder as defined in claim 416, wherein the conduit abuts and aligns with the disk space between the first vertebra and the second vertebra.

422. The holder as defined in claim 416, wherein the conduit is configured to allow tools and devices for implanting to pass therein.

423. The holder as defined in claim 416, wherein the body comprises a smooth outer surface.

424. The holder as defined in claim 416, wherein portions of the body reside on vertebral end caps during use.

425. The holder as defined in claim 416, wherein a height of the body is less than about six inches.

426. The holder as defined in claim 416, wherein a height of the body is less than about four inches.

427. The holder as defined in claim 416, wherein a height of the body is less than about two inches.

428. The holder as defined in claim 416, further comprising a hole in the body, the hole configured to receive a fastener that couples the body to the first vertebra.

429. The holder as defined in claim 428, wherein a centerline of the hole is angled oblique to a vertical axis of the body.

430. The holder as defined in claim 428, wherein the hole comprises a shoulder configured to limit insertion depth of the fastener through the body.

431. The holder as defined in claim 416, wherein the sleeve further comprises a view-port to provide increased visibility of a surgical site during use.

432. The holder as defined in claim 416, wherein the at least one protrusion is inserted between the first vertebra and the second vertebra to establish a separation distance between the vertebrae during use.

433. The holder as defined in claim 416, wherein the at least one protrusion comprises sides and further comprises serrations on at least one side of the at least one protrusion.

434. The holder as defined in claim 432, wherein an end of the at least one protrusion has a wedge shape.

435. The holder as defined in claim 432, wherein the at least one protrusion is configured to inhibit rotation of the body when the at least one protrusion is positioned in the disk space during use.

436. The holder as defined in claim 432, wherein the at least one protrusion comprises a surface to maintain parallel orientation of the adjacent vertebrae.

437. The holder as defined in claim 416, wherein the flange is made of a semi-rigid material.

438. A system for use during a spinal fusion procedure, comprising:
  a body, the body comprising a conduit through the body;
  a sleeve, wherein an end of the sleeve is removably positionable in the conduit;
  a slot in a wall of the conduit, the slot configured to engage a distractor on an end of the sleeve during use;
  at least one protrusion extending from the body; and
  wherein the conduit is configured to allow tools or devices for implanting a spinal fusion device, or for preparing a patient to receive a spinal fusion device, to be inserted in a disk space through the conduit.

439. The system of claim 438 wherein the body has a height of less than about six inches.

440. The system of claim 438, wherein the body has a height of less than about three inches.

441. The system of claim 438, wherein the body has a height of less than about two inches.

442. The system of claim 438, wherein portions of the body contact end caps of adjacent vertebrae during use.

443. The system of claim 438, wherein the body comprises a smooth outer surface.

444. The system of claim 438, further comprising a view-port in the sleeve, the view-port configured to be positioned adjacent to the body when the sleeve is positioned within the conduit to provide increased visibility of a surgical site during use.

445. The system of claim 438, further comprising a shoulder in the conduit, wherein the shoulder is configured to limit insertion depth of the sleeve into the conduit.

446. The system of claim 438, wherein a centerline of the conduit is parallel to a vertical axis of the body.

447. The system of claim 438, wherein a centerline of the conduit is angled oblique to a vertical axis of the body.

448. The system of claim 438, wherein the at least one protrusion is configured to maintain substantially parallel spacing between adjacent vertebrae when positioned within the disk space during use.

449. The system of claim 438, wherein the at least one protrusion is configured to inhibit rotation of the body when the at least one protrusion is positioned within the disk space during use.

450. The system of claim 438, wherein an end of the at least one protrusion has a wedge shape.

451. The system of claim 438, wherein the at least one protrusion further comprises serrations.

452. The system of claim 438, further comprising a flange removably coupled to the body, wherein the flange protects tissue and vessels adjacent to the body during use.

453. The system of claim 452, wherein the flange is made of a semi-rigid material.

454. The system of claim 452, wherein the flange comprises a collar configured to conform to the body to support the flange during use.

455. The system of claim 452, wherein a lower surface of the flange curves to substantially match surface curvatures of vertebrae located adjacent to the body during use.

456. The system of claim 438, further comprising a driver configured to be inserted into the sleeve and the disk space during use.

457. The system of claim 456, wherein the driver comprises:
   a shaft having a first end and a second end;
   a handle located proximate the second end;
   a coupling located proximate the first end;
   a removable attachment; and
   wherein the removable attachment is configured to couple to the coupling.

458. The system of claim 457, wherein the removable attachment comprises a drill bit.

459. The system of claim 457, wherein the removable attachment comprises a spinal implant.

460. The system of claim 457, wherein the driver further comprises a ridge on the shaft located proximate the second end, the ridge configured to limit insertion depth of the driver in the sleeve.

461. The system of claim 457, wherein the driver further comprises a collar on the shaft between the first end and the second end, the collar configured to be adjustable along the shaft to set a length of the driver that will pass into the sleeve.

462. The system of claim 461, wherein the collar comprises a lock, wherein engaging the lock fixably couples the collar to the shaft and inhibits movement of the collar with respect to the shaft.

463. A system for use during a spinal fusion procedure, comprising:
   a body, the body comprising a conduit through the body;
   a sleeve, wherein an end of the sleeve is removably positionable in the conduit;
   a shoulder in the conduit, the shoulder configured to limit insertion depth of the sleeve into the conduit;
   at least one protrusion extending from the body; and
   wherein the conduit is configured to allow tools or devices for implanting a spinal fusion device, or for preparing a patient to receive a spinal fusion device, to be inserted in a disk space through the conduit.

464. The system of claim 463, wherein the body has a height of less than about six inches.

465. The system of claim 463, wherein the body has a height of less than about three inches.

466. The system of claim 463, wherein the body has a height of less than about two inches.

467. The system of claim 463, wherein portions of the body contact end caps of adjacent vertebrae during use.

468. The system of claim 463, wherein the body comprises a smooth outer surface.

469. The system of claim 463, wherein a centerline of the conduit is parallel to a vertical axis of the body.

470. The system of claim 463, wherein a centerline of the conduit is angled oblique to a vertical axis of the body.

471. The system of claim 463, further comprising a view-port in the sleeve, the view-port configured to be positioned adjacent to the body when the sleeve is positioned within the conduit to provide increased visibility of a surgical site during use.

472. The system of claim 463, further comprising a flange removably coupled to the body, wherein the flange protects tissue and vessels adjacent to the body during use.

473. The system of claim 463, wherein the flange is made of a semi-rigid material.

474. The system of claim 463, wherein the flange comprises a collar configured to conform to the body to support the flange during use.

475. The system of claim 463, wherein a lower surface of the flange curves to substantially match surface curvatures of vertebrae located adjacent to the body during use.

476. The system of claim 463, wherein the at least one protrusion further comprises serrations on at least one side of the at least one protrusion, and wherein the at least one protrusion is configured to couple the body to a first vertebra and a second vertebra during use.

477. The system of claim 463, wherein the at least one protrusion is configured to establish a substantially parallel spacing between adjacent vertebrae when positioned within the disk space during use.

478. The system of claim 463, wherein the at least one protrusion is configured to inhibit rotation of the body when the at least one protrusion is positioned within the disk space during use.

479. The system of claim 476, wherein an end of the at least one protrusion has a wedge shape.

480. The system of claim 463, further comprising a driver configured to be inserted into the sleeve and the disk space during use.

481. The system of claim 480, wherein the driver comprises:
   a shaft having a first end and a second end;
   a handle located proximate the second end;
   a coupling located proximate the first end;
   a removable attachment; and
   wherein the removable attachment is configured to couple to the coupling.

482. The system of claim 481, wherein the removable attachment comprises a drill bit.

483. The system of claim 481, wherein the removable attachment comprises a spinal implant.

484. The system of claim 481, wherein the driver further comprises a ridge on the shaft located proximate the second end, the ridge configured to limit an insertion depth of the driver into the sleeve.

485. The system of claim 481, wherein the driver further comprises a collar on the shaft between the first end and the second end, the collar configured to be adjustable along the shaft to set a length of the driver that will pass into the sleeve.

486. The system of claim 485, wherein the collar comprises a locking means, wherein engaging the locking means fixably couples the collar to the shaft and inhibits movement of the collar with respect to the shaft.

487. A system for use during a spinal fusion procedure, comprising:
   a body, the body comprising a conduit through the body;
   a sleeve, wherein an end of the sleeve is removably positionable in the conduit;
   a view-port in the sleeve, the view-port configured to be positioned adjacent to the body when the sleeve is positioned within the conduit to provide increased visibility of a surgical site during use;
   at least one protrusion extending from the body; and
   wherein the conduit is configured to allow tools or devices for implanting a spinal fusion device, or for preparing a patient to receive a spinal fusion device, to be inserted in a disk space through the conduit.

488. The system of claim 487, wherein the body has a height of less than about six inches.

489. The system of claim 487, wherein the body has a height of less than about three inches.

490. The system of claim 487, wherein the body has a height of less than about two inches.

491. The system of claim 487, wherein portions of the body contact end caps of adjacent vertebrae during use.

492. The system of claim 487, wherein the body comprises a smooth outer surface.

493. The system of claim 487, wherein a centerline of the conduit is parallel to a vertical axis of the body.

494. The system of claim 487, wherein a centerline of the conduit is angled oblique to a vertical axis of the body.

495. The system of claim 487, wherein the at least one protrusion comprises serrations.

496. The system of claim 487, wherein the at least one protrusion is configured to establish a substantially parallel spacing between adjacent vertebrae when positioned within the disk space during use.

497. The system of claim 495, wherein the at least one protrusion is configured to inhibit rotation of the body when positioned within the disk space during use.

498. The system of claim 495, wherein an end of the at least one protrusion has a wedge shape.

499. The system of claim 487, further comprising a flange removably coupled to the body, wherein the flange protects tissue and vessels adjacent to the body during use.

500. The system of claim 499, wherein the flange is made of a semi-rigid material.

501. The system of claim 499, wherein the flange comprises a collar configured to conform to the body to support the flange during use.

502. The system of claim 499, wherein a lower, surface of the flange curves to substantially match surface curvatures of vertebrae located adjacent to the body during use.

503. The system of claim 491, further comprising a driver configured to be inserted into the sleeve and disc space during use.

504. The system of claim 503, wherein the driver comprises:
a shaft having a first end and a second end;
a handle located proximate the second end;
a coupling located proximate the first end;
a removable attachment; and
wherein the removable attachment is configured to couple to the coupling.

505. The system of claim 504, wherein the removable attachment comprises a drill bit.

506. The system of claim 504, wherein the removable attachment comprises a spinal implant.

507. The system of claims 504, wherein the driver further comprises a ridge on the shaft located proximate the second end, the ridge configured to limit an insertion depth of the driver into the sleeve.

508. The system of claim 504, wherein the driver further comprises a collar on the shaft between the first end and the second end, the collar configured to be adjustable along the shaft to set a length of the driver that will pass into the sleeve.

509. The system of claim 508, wherein the collar comprises a locking means, wherein engaging the locking means fixably couples the collar to the shaft and inhibits movement of the collar with respect to the shaft.

510. A method of inserting an implant during a spinal fusion procedure, comprising:
inserting a holder between a first vertebra and a second vertebra, wherein the first conduit extends through the holder from a top to a bottom of the holder;
securing the holder to the first vertebra and the second vertebra;
placing a sleeve into the first conduit of the holder;
preparing a space beneath the first conduit to receive a first implant with instruments inserted through the sleeve and through the first conduit; and
inserting an implant into the space through the first conduit.

511. The method as defined in claim 510, further comprising:
removing the sleeve from the first conduit of the holder;
placing a sleeve in a second conduit of the holder, the second conduit extending through the holder from the top to the bottom;
preparing a space beneath the second conduit to receive an implant with instruments inserted into the space beneath the second conduit through the sleeve and holder; and
inserting a second implant into the space beneath the second conduit through the second conduit.

512. The method as defined in claim 510, further comprising placing a flange about an outer surface of the holder after inserting the holder to shield surrounding tissue and vessels during use.

513. The method as defined in claim 510, wherein the holder comprises at least one distractor, and wherein inserting the holder comprises coupling a first end of a holder insertion device to the holder and hammering on a second end of the holder insertion device to drive the at least one distractor between the second vertebra and the first vertebra.

514. The method as defined in claim 510, wherein the holder comprises a first hole and a second hole through the holder, and wherein securing the holder to the first vertebra and the second vertebra comprises placing a first fastener in the first hole and inserting the first fastener into the first vertebra, placing a second fastener in the second hole and inserting the second fastener into the second vertebra.

515. The method as defined in claim 514, wherein the holder comprises a distractor extending from the bottom and positionable between the vertebrae to maintain a separation distance between the vertebrae.

516. The method as defined in claim 514, wherein thee first fastener is placed in the first hole and inserted through an end cap of the first vertebra and into cancellous bone of the first vertebra.

517. The method as defined in claim 514, wherein the second fastener is placed in the second hole and inserted through an end cap of the second vertebra and into cancellous bone of the second vertebra.

518. The method as defined in claim 510, wherein preparing the space comprises removing portions of end caps of the first and second vertebrae.

519. The method as defined in claim 518, wherein removing portions of the end caps comprises drilling portions of the end caps with a drilling tool inserted through the sleeve and through the first conduit.

520. The method as defined in claim 519, wherein preparing the space further comprises tapping the drilled portions of the vertebrae so that threading in the end caps will mate with threading of the implant.

521. The method as defined in claim 520, wherein inserting the implant comprises rotating the implant to advance the first implant into the tapped portion.

522. The method as defined in claim 518, wherein removing portions of the end caps comprises reaming portions of the end caps with a reaming tool inserted through the sleeve and through the first conduit.

523. The method as defined in claim 511, wherein preparing the space beneath the second conduit comprises removing portions of end caps of the first and second vertebrae.

524. The method as defined in claim 523, wherein removing portions of the end caps comprises drilling portions of the end caps with a drilling tool inserted through the sleeve and through the second conduit.

525. The method as defined in claim 523, wherein removing portions of the end caps comprises reaming portions of the end caps with a reaming tool inserted through the sleeve and through the second conduit.

* * * * *

UNITED STATES PATENT AND TRADEMARK OFFICE
CERTIFICATE OF CORRECTION

PATENT NO.   : 6,447,512 B1
DATED        : September 10, 2002
INVENTOR(S)  : Landry et al.

It is certified that error appears in the above-identified patent and that said Letters Patent is hereby corrected as shown below:

<u>Title page,</u>
Item [75], Inventors, delete "Hochshuler" and substitute therefor -- Hochshuler --.

<u>Column 16,</u>
Line 27, please delete "," before "second conduit".

<u>Column 21,</u>
Line 24, please delete "120" and substitute therefor -- 127 --.
Line 59, please delete "shoulders," and substitute therefor -- shoulder --.

<u>Column 25,</u>
Line 64, please insert -- wherein -- before "the opening".

<u>Column 26,</u>
Line 32, please delete "," before "shoulders configured".

<u>Column 27,</u>
Line 64, please delete "273" and substitute therefor -- 275 --.

<u>Column 28,</u>
Line 5, please delete "273" and substitute therefor -- 275 --.

<u>Column 29,</u>
Lines 25, 27, 30, 42, 44, 47, 51 and 55, please delete "281" and substitute therefor -- 297 --.

<u>Column 31,</u>
Line 57, please delete "334" and substitute therefor -- 344 --.

<u>Column 32,</u>
Line 27, please delete "wherein" and substitute therefor -- when --.

<u>Column 33,</u>
Line 2, please insert -- , -- after "conduit".
Line 7, please insert -- to a vertical axis of the body -- after "parallel".

UNITED STATES PATENT AND TRADEMARK OFFICE
CERTIFICATE OF CORRECTION

PATENT NO. : 6,447,512 B1
DATED : September 10, 2002
INVENTOR(S) : Landry et al.

It is certified that error appears in the above-identified patent and that said Letters Patent is hereby corrected as shown below:

<u>Column 35,</u>
Line 3, please insert -- , -- after "claim 393".
Line 41, please delete "416" and substitute therefor -- 417 --.

<u>Column 38,</u>
Lines 4, 6 and 9, please delete "463" and substitute therefor -- 472 --.

<u>Column 39,</u>
Line 36, please delete "," after "lower".
Line 39, please delete "491" and substitute therefor -- 487 --.
Line 40, please delete "disc" and substitute therefor -- disk --.
Line 55, please delete "claims" and substitute therefor -- claim --.

<u>Column 40,</u>
Line 49, please delete "thee" and substitute therefor -- the --.

Signed and Sealed this

Twenty-third Day of September, 2003

JAMES E. ROGAN
*Director of the United States Patent and Trademark Office*